US006261569B1

(12) United States Patent
Comis et al.

(10) Patent No.: US 6,261,569 B1
(45) Date of Patent: Jul. 17, 2001

(54) RETRO-, INVERSO- AND RETRO-INVERSO SYNTHETIC PEPTIDE ANALOGUES

(75) Inventors: Alfio Comis, Bossley Park; Margaret Isabel Tyler, Turramurra, both of (AU); Peter Fischer, Oslo (NO)

(73) Assignee: Deakin Research Limited, New South Wales (AU)

( * ) Notice: Subject to any disclaimer, the term of this patent is extended or adjusted under 35 U.S.C. 154(b) by 0 days.

(21) Appl. No.: 08/909,551

(22) Filed: Aug. 12, 1997

Related U.S. Application Data

(63) Continuation of application No. 08/387,932, filed as application No. PCT/AU93/00441 on Aug. 27, 1993, now abandoned.

(30) Foreign Application Priority Data

Aug. 27, 1992 (AU) .................................................. PL 4374

(51) Int. Cl.[7] ........................... G01N 33/53; A61K 39/29
(52) U.S. Cl. .................................... 424/204.1; 424/184.1; 424/185.1; 424/188.1; 424/190.1; 424/191.1; 424/208.1; 424/225.1; 424/227.1; 424/228.1; 424/236.1; 530/300; 530/332; 530/403; 530/806; 530/825; 530/826; 514/2
(58) Field of Search ........................ 424/208.1, 184.1, 424/185.1, 188.1, 204.1, 190.1, 191.1, 225.1, 227.1, 228.1, 236.1; 530/300, 332, 403, 806, 825, 826; 514/2

(56) References Cited

U.S. PATENT DOCUMENTS 4,010,260  3/1977  Immer et al. .

FOREIGN PATENT DOCUMENTS

| 10650/92 | 8/1992 | (AU) . |
| 1040623 | 1/1978 | (CA) . |
| 0 161 007 * | 1/1984 | (EP) ................ C07K/5/00 |
| 097994 | 1/1984 | (EP) . |
| 128602 | 12/1984 | (EP) . |
| 161007 | 11/1985 | (EP) . |
| 185433 | 6/1986 | (EP) . |
| 199379 | 10/1986 | (EP) . |
| 282891 | 9/1988 | (EP) . |
| 333356 | 9/1989 | (EP) . |
| 343460 | 11/1989 | (EP) . |
| 353565 | 2/1990 | (EP) . |
| 372670 | 6/1990 | (EP) . |
| 375040 | 6/1990 | (EP) . |
| 406931 | 1/1991 | (EP) . |
| WO87/07616 | 12/1987 | (WO) . |
| WO 89/06974 | 8/1989 | (WO) . |
| WO90/01494 | 2/1990 | (WO) . |
| WO91/13909 | 9/1991 | (WO) . |
| WO92/12247 | 7/1992 | (WO) . |
| WO93/11155 | 6/1993 | (WO) . |
| WO93/21218 | 10/1993 | (WO) . |
| WO 94/05311 | 3/1994 | (WO) . |

OTHER PUBLICATIONS

Lowell, et al.: Proteosomes–Lipopeptide vaccines: Enhancement . . . : Science: vol. 240: pp. 800–802, 1988.*
Haynes: Scientific and social issues of Human Immunodeficiency Virus . . . : Science: vol. 260: pp. 1279–1286, 1993.*
Cohen: Jitters Jeopardize AIDS Vaccine Trials: Science: vol. 262: pp. 980–981, 1993.*
Briand, et al.: A retro–inverso peptide corresponding . . . : Proc. Natl. Acad. Sci.: vol. 94: pp. 12545–12550, Nov. 1997.*
Benikrane, et al.: Mimicry of viral epitopes with retro–inverso . . . : Dev. Bio. Stand.:87: abstract, 1996.*
Van Regenmortel, et al.: The potential of retro–inverso peptides . . . : Dev. Bio. Stand: abstract, 1998.*
M. Rodriguez et al, "Synthesis and Biological Activity of Some Partially Modified Retro–Inverso Analogues of Cholecystokinin", *J. Med. Chem.*, 32(10):2331–2339 (1989).
H. Kessler et al, "Peptide Conformation—Conformation and Biological Activity of Proline Containing Cyclic Retro–Analogues of Somatostatin", *Int. J. Peptide Protein Res.*, 31(5):481–498 (1988).
D. Lelievre et al, "Synthesis and Characterization of Retro Gramicidin A–DAla–Gramicidin A, a 31–residue–long Gramicidin Analogue", *Int. J. Peptide Protein Res.*, 33(5):379–385 (1989).
J. Berman et al, "Receptor Binding Affinity and Thermolysin Degradation of Truncated and Retro–Inverso–Isomeric ANF Analogs", *Life Sciences*, 44(18):1267–1270 (1989).
P. Guptasarma, "Reversal of Peptide Backbone Direction May Result in the Mirroring of Protein Structure", *FEBS Letters*, 310(3):205–210 (Oct. 1992).
M. Chorev et al, "A Dozen Years of Retro–Inverso Peptidomimetics", *Acc. Chem. Res.*, 26(5):266–273 (May 1993).
F. DeAngelis et al, "Fast Atom Bombardment Mass Spectrometry and Selective Acid Hydrolysis for the Analysis of Partially Modified Retro–Inverso Peptide Analogues", *Biomed. Environ. Mass Spectrometry*, 18(10):867–871 (1989).
M. Cushman et al, "Synthesis, Biological Testing, and Stereochemical Assignment of an End Group Modified Retro–Inverso Bombesin C–Terminal Nonapeptide", *J. Org. Chem.*, 55(10):3186–3194 (1990).

(List continued on next page.)

*Primary Examiner*—Marianne P. Allen
*Assistant Examiner*—Mary K. Zeman
(74) *Attorney, Agent, or Firm*—Howson and Howson

(57) ABSTRACT

Synthetic peptide antigen analogues of native peptide antigens with partial or complete retro, inverso or retro-inverso modifications are provided. When administered as an immunogen to an immunocompetent host the synthetic peptide antigen analogues induce the production of antibodies which recognize the native peptide antigen. Uses of these analogues, vaccines and methods of preparing vaccines comprising these antigen analogues, and antibodies generated using these antigen analogues are also provided.

16 Claims, 10 Drawing Sheets

OTHER PUBLICATIONS

E. Schroder et al, "Synthesis, Occurrence, and Action of Biologically Active Polypeptides", *The Peptides*, vol. II, Academic Press, New York (1966).

D. Davies et al, "Antibody–Antigen Complexes", *J. Biol. Chem.*, 263(22):10541–10544 (Aug. 5, 1988).

A. Verdini et al, "Synthesis, Resolution, and Assignment of Configuration of Potent Hypotensive Retro–Inverso Bradykinin Potentiating Peptide 5a(BPP5a) Analogues", *J. Chem. Soc. Perkin Trans.*, pp. 697–701 (1985).

M. Steward et al, "Synthetic Peptides: A Next Generation of Vaccines?", *Immunology Today*, 8(2):51–58 (1987).

R. Arnon, "Synthetic Peptides as the Basis for Vaccine Design", *Mol. Immunol.*, 28(3):209–215 (1991).

M. Mariani et al, "Immunogenicity of a Free Synthetic Peptide: Carrier–Conjugation Enhances Antibody Affinity for the Native Protein", *Mol. Immunol.*, 24(3):297–303 (1987).

F. Bonelli et al, "Solid Phase Synthesis of Retro–Inverso Peptide Analogues", *Int. J. Peptide Protein Res.*, 24:553–556 (1984).

R. Lerner, "Antibodies of Predetermined Specificity in Biology and Medicine", *Advances in Immunology*, 36:1–44 (1984).

M. Goodman et al, "The Synthesis and Conformational Analysis of Retro–Inverso Analogues of Biologically Active Molecules", *Perspectives in Peptide Chemistry*, pp. 283–294, Karger, Basel (1981).

F. DeAngelis, "The Mass Spectrometric Determination of Retro–Inverso Linear Peptides", *NATO ASI Series, Series C: Mathematical and Physical Sciences*, 353:357–369 (Jan. 1992).

H. Durr et al, "Retro–Inverso Amide Bonds Between Trifunctional Amino Acids", *Angew. Chem. Int. Ed. Engl.*, 31(6):785–787 (1992).

N. Benkirane et al, "Antigenicity and Immunogenicity of Modified Synthetic Peptides Containing D–Amino Acid Residues", *J. Biol. Chem.*, 268(35):26279–26285 (Dec., 1993).

G. Guichard et al, "Antigenic Mimicry of Natural L–Peptide with Retro–Inverso–Peptidomimetics", *Proc. Natl. Acad. Sci. USA*, 91:9765–9769 (Oct., 1994).

A. Sette et al., "Effect of Conformational Propensity of Peptide Antigens in Their Interaction with MHC Class II Molecules", *J. Immunol.*,(4):1268–1273 (Aug., 1989).

M. Good et al, "Construction of Synthetic Immunogen: Use of New T–Helper Epitope of Malaria Circumsporozoite Protein", *Science*, 235:1059–1062 (Mar., 1988).

M. Good et al, "Parasite Polymorphism Present within Minimal T Cell Epitopes of Plasmodium falciparum Circumsporozoite Protein", *J. Immunol.*, 140(5):1645–1650 (Mar., 1988).

K. Kim et al, "Determination of T Cell Epitopes on the S1 Subunit of Pertussis Toxin", *J. Immunol.*, 144(9):3529–3534 (May, 1990).

F. Sinigaglia et al, "A Malaria T–Cell Epitope Recognized in Association with Most Mouse and Human MHC Class II Molecules", *Nature*, 336:778–780 (Dec., 1988).

M. Francis et al, "Immunological Priming with Synthetic Peptides of Foot–and–Mouth Disease Virus", *J. Gen. Virol.*, 66:2347–2354 (1985).

C. Hackett et al, "Influenza Virus Site Recognized by a Murine Helper T Cell Specific for H1 Strains", *J. Exp. Med.*, 158:294–302 (Aug., 1983).

J. Hurwitz et al, "Characterization of the Murine TH Response to Influenza Virus Hemagglutinin: Evidence for Three Major Specificities", *J. Immunol.*, 133(6):3371–3377 (Dec., 1984).

J. Lamb et al, "Human T–Cell Clones Recognized Chemically Synthesized Peptides of Inlfuenza Haemagglutinin", *Nature*, 300:66–69 (Dec., 1984).

R. Macfarlan et al, "T Cell Responses to Cleaved Rabies Virus Glycoprotein and to Synthetic Peptides", *J. Immunol.*, 133(5):2748–2752 (Nov., 1984).

D. Milich et al, "Genetic Regulation of the Immune Response to Hepatitis B Surface Antigen (HbsAg)", *J. Immunol.*, 134(6):4203–4211 (Jun., 1985).

D. Milich et al, "T and B Cell Recognition of Native and Synthetic Pre–S Region Determinants of HbsAg", Abstract presented at the Sep. 11–Sep. 15, 1985 meeting on *Modern Approaches to Vaccines*, Cold Spring Harbor Laboratory, Cold Spring Harbor, NY (1985).

J. Nicholas et al, "Mapping An Antibody–Binding Site and a T–Cell–Stimulating Site on the 1A Protein of Respiratory Syncytial Virus", *J. Virol.*, 62(12):4465–4473 (Dec., 1988).

C. Partidos et al, "Immune Responses in Mice Following Immunization with Chimeric Synthetic Peptides Representing B and T Cell Epitopes of Measles Virus Protein", *J. Gen. Virol.*, 72:1293–1299 (1991).

A. Rosenthal, "Determinant Selection and Macrophage Function in Genetic Control of the Immune Response", *Immunol. Rev.*, 40:135–152 (1978).

J. Thomas et al, "Immune Response Gene Control of Determinant Selection, III. Polypeptide Fragments of Insulin are Differentially Recognized by T but not by B Cells in Insulin Immune Guinea Pigs", *J. Immunol.*, 126(3):1095–1100 (Mar., 1981).

M. Jolivet et al, "Polyvalent Synthetic Vaccines: Relationship Between T Epitopes and Immunogenicity", *Vaccine*, 8:35–40 (Feb., 1990).

R. Schwartz, "The Value of Synthetic Peptides as Vaccines for Eliciting T–Cell Immunity", *Current Topics in Microbiology and Immunology*, 130:79–85 (1986).

G. Fasman et al, "Conformational Analysis of the Immuno–dominant Epitopes of the Circumsporozoite Protein of Plasmodium Faciparum and knowlesi", *Biopolymers*, 29:123–130 (1990).

V. Van Cleave et al, "Do Antibodies Recognize Amino Acid Side Chains of Protein Antigens Independently of the Carbon Backbone?", *J. Exp. Med.*, 167:1841–1848 (Jun., 1988).

H. Geysen, "Antigen–Antibody Interactions at the Molecular Level: Adventures in Peptide Synthesis", *Immunology Today*, 6(12):364–369 (1985).

J. Klasse et al, "Differential IgG Subclass Responses to Epitopes in Transmembrane Protein of HIV–1", *Viral Immunology*, 3(2):89–98 (1990).

D. Wade et al, "All–D Amino Acid–Containing Channel–Forming Antibiotic Peptides", *Proc. Natl. Acad. Sci. USA*, 87:4761–4765 (Jun., 1990).

* cited by examiner

RETRO-, INVERSO- AND RETRO-INVERSO SYNTHETIC PEPTIDE ANALOGUES

This application is a continuation of application Ser. No. 08/387,932, filed Apr. 24, 1995, now abandoned, which is a 371 of PCT/AU93/00441, filed Aug. 27, 1993.

TECHNICAL FIELD

The invention relates to synthetic peptide antigen analogues of native peptide antigens with partial or complete retro, inverso or retro-inverso modifications. When administered as an immunogen to an immunocompetent host the synthetic peptide antigen analogues induce the production of antibodies which recognize the native peptide antigen. The invention also relates to uses of these analogues, to vaccines and methods of preparing vaccines comprising these antigen analogues, and to antibodies generated using these antigen analogues.

BACKGROUND ART

The stereochemistry of polypeptides can be described in terms of the topochemical arrangement of the side chains of the amino acid residues about the polypeptide backbone which is defined by the peptide bonds between the amino acid residues and the α-carbon atoms of the bonded residues. In addition, polypeptide backbones have distinct termini and thus direction.

The majority of naturally occurring amino acids are L-amino acids. Naturally occurring polypeptides are largely comprised of L-amino acids.

D-amino acids are the enantiomers of L-amino acids and form peptides which are herein referred to as inverso peptides, that is, peptides corresponding to native peptides but made up of D-amino acids rather than L-amino acids.

Retro peptides are made up of L-amino acids in which the amino acid residues are assembled in opposite direction to the native peptide sequence.

Retro-inverso modification of naturally occurring polypeptides involves the synthetic assemblage of amino acids with α-carbon stereochemistry opposite to that of the corresponding L-amino acids, i.e. D- or D-allo-amino acids, in reverse order with respect to the native peptide sequence. A retro-inverso analogue thus has reversed termini and reversed direction of peptide bonds while approximately maintaining the topology of the side chains as in the native peptide sequence.

Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively.

Processes for synthesis of retro-inverso peptide analogues (Bonelli et al., 1984; Verdini and Viscomi, 1985) and some processes for the solid-phase synthesis of partial retro-inverso peptide analogues have been described (Pessi et al., 1987).

It has been observed that due to the stereospecificity of enzymes with respect to their substrates, replacement of L-amino acid residues with D-amino acid residues in peptide substrates generally abolishes proteolytic enzyme recognition and/or activity, although exceptions are known.

Peptide hormones have been of particular interest as targets for retro-inversion, presumably because their analogues would have potential use as therapeutic agents.

Partial, and in a few cases complete, retro-inverso analogues of a number of peptide hormones have been prepared and tested (see, for example, Goodman and Chorev, 1981).

Complete or extended partial retro-inverso analogues of hormones have generally been found to be devoid of biological activity. The lack of biological activity has been attributed to possible complex structural changes caused by extended modification, the presence of reversed chain termini or the presence of proline residues in the sequences. Some partial retro-inverso analogues, that is peptides in which only selected residues were modified on the other hand, have been shown to retain or enhance biological activity. Retro-inversion has also found application in the area of rational design of enzyme inhibitors.

The fact that retro-inversion of biologically active peptides has met with only limited success in retaining or enhancing the activity of the native peptide is probably due to several reasons. Although structurally very similar, it was realized early that peptides and their retro-enantiomers are topologically not identical and crystal structure and solution conformation studies have borne this out. Biological activity of a peptide hormone or neurotransmitter depends primarily on its dynamic interaction with a receptor, as well as on transduction processes of the peptide-receptor complex. It is now clear that such interactions are complex processes involving multiple conformational and topological properties. Consequently it is not surprising that a retro-inverso analogue may not be able to mimic all of these properties.

The development of synthetic peptide vaccines has been a very active field of research over the past two decades (Arnon, 1991; Steward and Howard, 1987). Unfortunately, not much is known about the chemistry of antigen-antibody binding; only very few X-ray crystal structures of antibody-antigen complexes have been solved to date (Davies et al., 1988). As a result, prior to the present invention, it was not possible to predict if antibodies could be elicited against an inverso, retro or retro-inverso peptide and if such antibodies would be capable of recognizing the native peptide antigen from which the peptide sequence was derived. Lerner and co-workers (Lerner, 1984) report the synthesis of native, retro-, inverso- and retro-inverso forms of an influenza virus haemagglutinin peptide. They claim that antibodies raised against these peptides are not cross-reactive and that only antibodies against the native form peptide bind to the native peptide antigen.

Oral immunization, with the production of secretory immunoglobulin A (IgA) antibodies in various mucosae, has been used for many years, particularly for gastrointestinal infections. Successful induction of a systemic immune response to an orally administered polypeptide antigen requires that at least some of the antigen is taken up into the circulation. It is now known that intestinal peptide transport is a major process, with the terminal stages of protein digestion occurring intracellularly after non-specific transport of peptides into the mucosal absorptive cells. There is also irrefutable evidence that small amounts of intact peptides and proteins do enter the circulation from the gut under normal circumstances. Due to inefficient is intestinal absorption and due to proteolytic degradation of 'native' polypeptide antigens, the amount of antigen required for oral immunization generally far exceeds that required for parenteral induction of systemic immunity. Furthermore, oral presentation of such large quantities of antigen often leads to the simultaneous induction of IgA/suppressor T-cell-mediated systemic tolerance which acts to reduce the production of immunoglobulin G (IgG) antibodies. Therefore, a need exists for non-tolerogenic effective oral vaccines which can withstand proteolytic attack.

DISCLOSURE OF THE INVENTION

Definitions

Throughout the specification and claims "retro modified" refers to a peptide which is made up of L-amino acids in which the amino acid residues are assembled in opposite direction to the native peptide with respect the which it is retro modified.

Throughout the specification and claims "inverso modified" refers to a peptide which is made up of D-amino acids in which the amino acid residues are assembled in the same direction as the native peptide with respect to which it is inverso modified.

Throughout the specification and claims "retro-inverso modified" refers to a peptide which is made up of D-amino acids in which the amino acid residues are assembled in the opposite direction to the native peptide with respect to which it is retro-inverso modified.

Throughout the specification and claims the term "native" refers to any sequence of L amino acids used as a starting sequence for the preparation of partial or complete retro, inverso or retro-inverso analogues.

The term "peptide" as used throughout the specification and claims is to be understood to include peptides of any length.

Throughout the specification and claims the term "antigenic fragment" refers to a peptide which is a portion of an antigen which itself is immunogenic or capable of binding antibodies.

The term "antigen" as used throughout the specification and claims is to be understood to include immunogens as the context requires.

Throughout the specification and claims the term "antigen analogue" refers to a peptide molecule capable of mimicking the immunological activity of the native peptide antigen with respect to which it is partially or completely retro, inverso or retro-inverso modified.

Partial modification refers to an analogue in which a part of the native peptide is modified. The part(s) modified must include at least one minimum antigenic fragment capable of producing and/or binding antibodies. Such fragments are variable in length so that partially modified analogues can include analogues in which as few as two consecutive residues are modified. Typically at least 5 or 6 consecutive residues are modified.

Other amino acids, usually, but not restricted to L isomers, can be added to the antigen peptide for purposes such as conjugation or increasing solubility. Cysteine can be included as its Acm derivative to prevent polymerization or cyclization of a peptide or replaced by amino butyric acid.

The present invention relates to partially or completely retro, inverso or retro-inverso modified antigen analogues of native peptide antigens which, when administered to an immunocompetent host as an immunogen, induce the production of antibodies which recognize the native antigen. Surprisingly, the antigen analogues in accordance with the invention have been shown to have immunological activity and are therefore candidates for the preparation of vaccines. Incorporation of D-amino acids into peptide antigen analogues increases their stability to degradation after administration. Further, incorporation of D-amino acids has potential for oral administration of analogues. Having shown that antibodies can be elicited against retro, inverso and retro-inverso antigen analogues, which are capable of recognizing the native peptide antigen from which the sequence of the analogue was derived, it follows that generally retro, inverso and retro-inverso antigen analogues can be expected to be successful since antibody-antigen binding interactions are not fundamentally different from case to case.

According to a first aspect of the present invention, there is provided a synthetic peptide antigen analogue of a native peptide antigen, which analogue is partially or completely retro modified with respect to the native antigen.

According to a second aspect of the present invention there is provided a synthetic peptide antigen analogue of a native peptide antigen, which analogue is partially or completely inverso modified with respect to the native antigen.

According to a third aspect of the present invention, there is provided a synthetic peptide antigen analogue of a native peptide antigen, which analogue is partially or completely retro-inverso modified with respect to the native antigen. The analogues of the invention induce the production of antibodies which recognize the native peptide antigen when administered as an immunogen to an immunocompetent host. In the case of retroinverso analogues it is recognized that further modification can be required in special cases. Where the chosen peptide antigen is smaller than the average size of an antibody-binding antigenic structure, then the C and N-terminal groups will be as important as the internal residues in recognition of and binding to the antibody. A completely retro-inverso version of such a peptide antigen is likely to differ sufficiently from the native peptide antigen at its ends to render it ineffective as an antigen analogue. For such peptides it is desirable to either produce polymers made up of multiple copies of the peptide or modify the ends of the peptides by protecting them with, for instance, additional residues joined to them or chemically replacing them by side-chain-analogous-substituted geminal diaminomethanes and malonates. Other techniques such as cyclizing these peptides may also be beneficial.

Typically, the antibodies raised are capable of neutralizing deleterious biological activity of the native peptide antigens, however, it is to be understood that antibodies raised against the analogues of the invention which are able to bind the native peptide antigen, whether or not they are also capable of such neutralization are of use, for instance, in diagnostic applications. Given that the antigen analogues of the invention lead to production of antibodies which recognize the native antigen it follows that they are candidates for vaccine components in situations where vaccination against a native antigen is desirable. It is recognized that in some individuals in a population of test animals a portion will fail to respond to immunization because of major histocompatibilty complex (MHC) restriction. However those members of the population which do respond, respond very well. This lack of response is a common immunological phenomenon and should not be considered to be an indication that retroinverso antigen analogues have variable efficacy.

The invention also encompasses the antigen analogues of the invention when used to immunize an immunocompetent host.

According to a fourth aspect of the present invention there is provided a vaccine comprising at least one antigen analogue of the present invention together with a pharmaceutically or veterinarally acceptable carrier, diluent, excipient and/or adjuvant.

Vaccines of the invention may comprise antigen analogues conjugated with a suitable carrier or synthesized with the analogue and a proteinaceous carrier forming a continuous polypeptide.

Vaccines of the invention can be formulated using standard methods in the art of vaccine formulation.

Selection of appropriate diluents, carriers, excipients and/or adjuvants can be made in accordance with standard techniques in the art.

Preferably, those synthetic peptide antigen analogues of the invention containing D-amino acids are capable of eliciting immune responses which last longer than the immune response obtained with the corresponding native antigen.

Typically the native antigen is any naturally occurring polypeptide or antigenic fragment thereof, which is capable of eliciting an immune response in a host. Native antigens in accordance with the invention include peptides or polypeptides of any length whose amino acid sequences stem from polypeptides of pathogens such as poliomyelitis, hepatitis B, foot and mouth disease of livestock, tetanus, pertussis, HIV, cholera, malaria, influenza, rabies or diptheria causing agents, or toxins such as robustoxin, heat labile toxin of pathogenic *Escherichia coli* strains and Shiga toxin from *Shigella dysenteriae*. Other antigens of interest include Amyloid β protein (Alzheimer's disease) and human chorionic gonadotropin and gonadotropin releasing hormone (contraceptive vaccines).

Preferred analogues of the invention are analogues of the malarial antigen which is the immunodominant epitope of the circumsporozoite coat protein of *P. falciparum* sporozoites or a diphtheria toxin antigen or an HIV-1 antigen, HBV antigen or robustoxin. More preferably the analogues are retro-inverso forms of these molecules.

Vaccines of the invention may be administered to hosts in need of such treatment by injection. Vaccines incorporating D-amino acid containing analogues may also be administered orally. When the vaccine is to be administered by injection the antigen analogue can be conjugated to an appropriate carrier molecule and injected via conventional methods for example intramuscularly.

The present invention also provides a method of vaccinating a host in need of such treatment which method comprises administering an effective amount of an antigen analogue or vaccine according to the invention to the host.

In a further aspect of the invention, antibodies produced by immunization of a host with antigen analogues of the invention are provided. These antibodies are useful as agents in the diagnosis, treatment and/or prophylaxis of diseases, as well as drug delivery.

The invention also provides a method of analysis of a sample for antibodies to a native peptide antigen comprising using an antigen analogue of the antigen according to the invention.

The invention additionally provides a method of analysis of a sample for the presence of a native peptide antigen comprising using antibodies of the invention which recognize the antigen.

The invention further provides a diagnostic kit comprising at least one antigen analogue or antibody of the invention, together with positive and negative control standards. Where the kit is to be used to detect antibodies to a particular native antigen, the kit will comprise an antigen analogue of the native antigen. The positive standard may be an antibody of the invention raised to that antigen analogue. The negative standard may be any non-cross-reacting antibody. Where the diagnostic kit is to be used for the detection of a native antigen, the kit will comprise antibody to an analogue of the native antigen. The analogue of the native antigen may be used as the positive standard. A peptide not recognized by the antibody is used as negative standard.

The invention also provides a method of preparing an antigen analogue, of a native peptide antigen comprising synthesizing a partially or completely retro, inverso or retro-inverso analogue of the native peptide antigen.

Other amino acids, usually, but not restricted to L isomers, can be added to the antigen peptide for purposes such as conjugation or increasing solubility. Cysteine can be included as its Acm derivative to prevent polymerization or cyclization of a peptide or replaced by amino butyric acid.

The invention further provides a method of preparing a vaccine against a native peptide antigen which method comprises: providing a retro, inverso or retro-inverso analogue of the native peptide antigen; and admixing an effective amount of the antigen analogue with a pharmaceutically or veterinarally acceptable carrier, diluent excipient and/or adjuvant. The method of preparing a vaccine may additionally comprise conjugating the antigen analogue to a suitable carrier molecule.

ABBREVIATIONS

Ab Antibody
BOP (benzotriazolyloxy)tris(dimethylamino) phosphonium hexafluorophosphate (Castro's reagent)
DMF dimethyl formamide
BSA bovine serum albumin
ELISA enzyme-linked immunosorbent assay
Fmoc 9-fluorenylmethoxycarbonyl
HPLC high-performance liquid chromatography
Ig immunoglobulin
in inverso
i.p. intraperitoneal
KLH keyhole limpet haemocyanin
Mod model
no normal (native)
PBS phosphate buffered saline (10 mM phosphate, 150 mM NaCl, pH 7.4)
Pfp pentafluorophenyl
PVC polyvinylchloride
re retro
ri retro-inverso
TFA trifluoroacetic acid
Amino Acids
L-amino acids are indicated by an upper case followed by lower case lettering e.g. Ala indicates L-alanine.
D-amino acids are indicated by all lower case abbreviations, e.g. ala indicates D-alanine.

BEST MODE OF CARRYING OUT THE INVENTION

Figure 1:
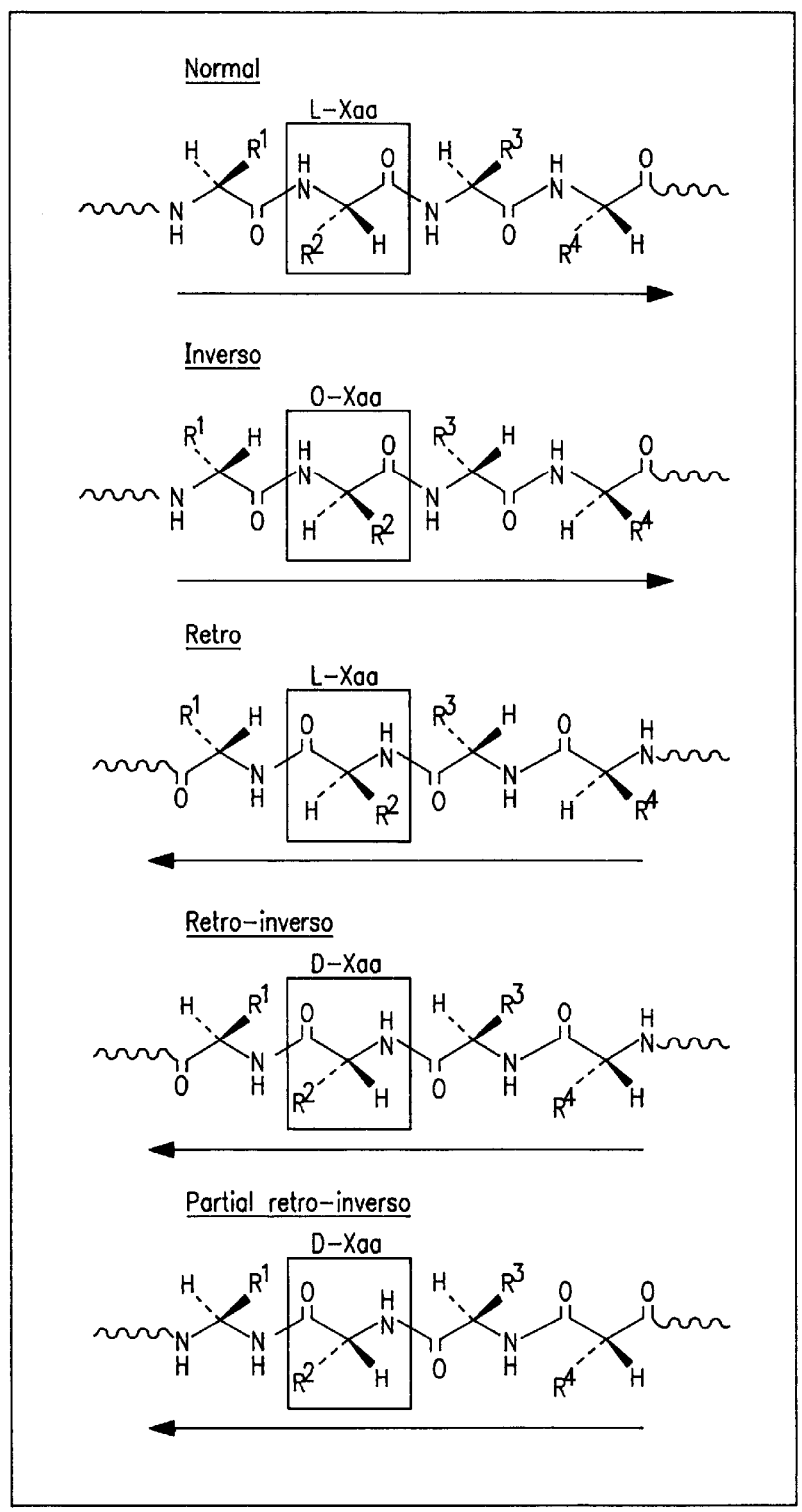
FIG. 1 illustrates modifications which can be made to an amino acid sequence in accordance with the present invention. $R^1$, $R^2$, $R^3$ and $R^4$ represent amino acid side chains, and Xaa represents any amino acid residue.

Antigen analogues of the invention are prepared by standard techniques for the preparation of L and D amino acid containing peptides, particularly as outlined in Example 1.

Vaccines of the invention are formulated by standard techniques for vaccine formulation using standard carriers, diluents, excipients and/or adjuvants suitable for the formulation of oral or injectable vaccines. Effective amounts of antigen analogues to be incorporated in the vaccines can be determined in accordance with standard methods.

The vaccination regimes used are standard regimes for the vaccination of animal or human hosts. These regimes can be used where immunization of the host is desired or where the host is being used to produce antibodies for exogenous use. Diagnostic kits of the invention are prepared by standard methods for the preparation of the reagents and controls of such kits.

Generally the diagnostic kits are in radio immunoassay (RIA) or immunofluorescence or ELISA formats: the latter can be carried out as described in Example 4.

Where the analogues or antibodies raised against them are used in the detection of a native antigen or an antibody against it, the appropriate agent can be used in immunoassay format against a sample to be tested with appropriate controls.

The invention is further described in the following examples which are illustrative of the invention but in no way limiting on its scope.

The following examples show that antigen analogues in accordance with the invention surprisingly can elicit antibodies capable of recognizing the native sequence, not only in the form of a peptide, but also when contained in the protein from which it was derived. Three antigen sequences were chosen and tested for their ability to produce antibodies capable of recognizing and interacting with the parent native sequence (Examples 5, 6 and 7). One antigen sequence (Example 5) was a model without biological relevance, while the other two antigen sequences (Examples 6 and 7) represent synthetic peptide antigens whose potential usefulness as vaccines against malaria and diphtheria, respectively, has been demonstrated previously. The observed cross-reactivity of antibodies against 'native' and retro-inverso peptides strongly indicates that antibodies recognize antigens primarily by the constellation of their amino acid side chains independently of their backbone. In all three cases studied polyclonal antibody preparations against retro-inverso peptide antigens appeared to bind equally well to the parent sequence and to the retro-inverted antigen.

Conventional immunization with retro-inverso antigens conjugated to carrier proteins, and oral immunization with free retro-inverso antigens, are shown to be feasible. The ability to induce cross-reactive serum antibodies to retro-inverso antigens indicates the utility of such antigens as vaccines. As demonstrated, these antigens are amenable to immunization without carrier proteins, not only by injection, but also by oral administration. Probably this is dependent on at least one T-cell epitope being present. This observation, together with the finding that the immune response to retro-inverso antigens is relatively long-lived, indicate the utility of these analogues in overcoming the two main problems of existing experimental synthetic peptide vaccines.

Example 1

Peptide Synthesis

Peptides were synthesized by a solid-phase method, on polyamide (Arshady et al., 1981) or Polyhipe supports using side-chain protected Fmoc amino acids (Carpino & Han, 1972), essentially as described by Eberle et al. (1986). Only pure amino acid derivatives, obtained commercially or by synthesis, were used. The polyamide synthesis resins, derivatized with p-alkoxybenzyl alcohol-based linkage agents, were esterified quantitatively with the appropriate preformed C-terminal Fmoc-amino acid symmetrical anhydrides, in the presence of 0.2 molar equivalents of N,N-dimethylaminopyridine and N-methylmorpholine. The Polyhipe resin derivatized with Fmoc-Rink linker (Rink, 1987) did not require esterification of the first amino acid to it. Chain elongation was carried out using Fmoc-amino acid pentafluorophenyl esters (Atherton et al., 1988) or Castro's reagent/1-hydroxybenzotriazole coupling (Hudson, 1988). The progress of each synthesis was monitored using a specific color test (Hancock & Battersby, 1976) and/or amino acid analysis of acid-hydrolyzed peptidyl resin samples.

The peptides were cleaved from the resins and side-chain deprotected with the aid of TFA, containing a suitable mixture of scavenger chemicals (Tam, 1988). After filtration and vacuum evaporation, the peptides were triturated with diethyl ether, collected by centrifugation and lyophilized from aqueous ammonium bicarbonate solution.

All peptides then underwent an initial desalting and purification step by column chromatography on suitable gel filtration media in aqueous solvents. Afterwards they were purified to homogeneity by reversed-phase HPLC using water-acetonitrile (containing 0.05–0.1% TFA) gradient elution. The purity of the synthetic peptides was further assessed by gas-phase acid hydrolysis/amino acid analysis (Bidlingmeyer et al., 1987) and, if deemed necessary, by automated gas-phase sequencing (Hunkapiller & Hood, 1983).

Example 2

Peptide-carrier Protein Conjugation

Synthetic peptides were coupled via their cysteine thiol groups to carrier proteins using a method adapted from Liu et al. (1979), as follows:

KLH (40 mg) or BSA (100 mg) was dissolved in 3mL 50 mM phosphate buffer, pH 6.0. m-Maleimidobenzoyl-N-hydroxysuccinimide ester (MBS; 0.2 mL of a fresh 25 mg/mL stock solution in N,N-dimethylformamide) was added slowly and the mixture stirred at room temperature for 30 min. It was then immediately filtered through a 0.8 mm membrane and pumped onto a column (11×170 mm) of Sephacryl S-300. This was developed at 0.25 mL/min with pH 6 buffer. The protein-MB-containing fractions were collected, pooled and added to prepared peptide solution (10 μmol in pH 7.5 phosphate buffer). The pH of this mixture was adjusted to 7.5 with 0.1M NaOH; it was then flushed with nitrogen, sealed and stirred magnetically for 2.5 h. After exhaustive dialysis ($M_r$ 12,000–15,000 cut-off) against dilute ammonium bicarbonate, the protein-carrier protein conjugates were isolated by lyophilization. All aqueous solution were degassed prior to use.

Example 3

Immunisation

Young Swiss albino mice were used for immunization. Intraperitoneal (i.p.) injections of peptide-KLH conjugates were made without any adjuvant. Oral immunizations were carried out by feeding starved mice with food pellets into which the appropriate antigen solution had been soaked.

Example 4

ELISA Procedures

The wells of PVC microtitre plates were coated with the appropriate antigen (0.25–10 μg/well), dissolved in dilute carbonate/bicarbonate buffer, pH 9.2, overnight at 4° C. After aspiration, blocking was effected by incubation for 2 h with 4% BSA or boiled casein, 0.05% Tween-20 in PBS. The wells were then washed several times with 0.1% Tween-20 in PBS before addition of antiserum, serially diluted in blocking solution. After incubation for 4 h, the plates were again washed. Bound IgG was detected by incubation for 1 h with suitably diluted (in blocking solution) affinity-purified anti-mouse IgG-horseradish peroxidase, washing and development with 0.5 mg/mL o-phenylenediamine, 0.01% peroxide at pH 5 in the dark. Color development was stopped by the addition of 4M sulphuric acid. The plates were then read immediately at a wavelength of 492 nm.

All incubation steps, with the exception of coating, were carried out at room temperature and with agitation of the plates.

Example 5

Analysis of Antibody Production and Activity of Antibodies Raised to a Synthetic Antigen Sequence Without Biological Relevance The following model dodecapeptides were synthesized using cysteine thiol protection as the trityl thioether and cleavage of peptidyl resin with 5% thiophenol in TFA for 90 min. Protein conjugates were prepared for the purposes of immunization.

Normal (native) peptide (L-amino acids, N→C direction) noMod: H-Gly-Cys-Gly-Pro-Leu-Ala-Gln-Pro-Leu-Ala-Gln-Gly-OH (SEQ ID No.1)

Retro-inverso peptide (D-amino acids, C→N direction) riMod: H-Gly-gln-ala-leu-pro-gln-ala-leu-pro-Gly-Cys-Gly-OH Retro peptide (L-amino acids, C→N direction) remod: H-Gly-Gln-Ala-Leu-Pro-Gln-Ala-Leu-Pro-Gly-Cys-Gly-OH (SEQ ID No.2)

Inverso peptide (D-amino acids, N→C direction) inMod: H-Gly-Cys-Gly-pro-leu-ala-gln-pro-leu-ala-gln-Gly-OH Intraperitoneal Immunization Groups of four mice per antigen were immunized intraperitoneally with 0.2 mg/dose of KLH-peptide in 0.1 mL PBS. Boosters were given 4, 9 and 16 days later. Anti-peptide antibodies in the pooled sera (from each group) were measured in an ELISA using immobilized BSA-peptide conjugates.

Figure 2:
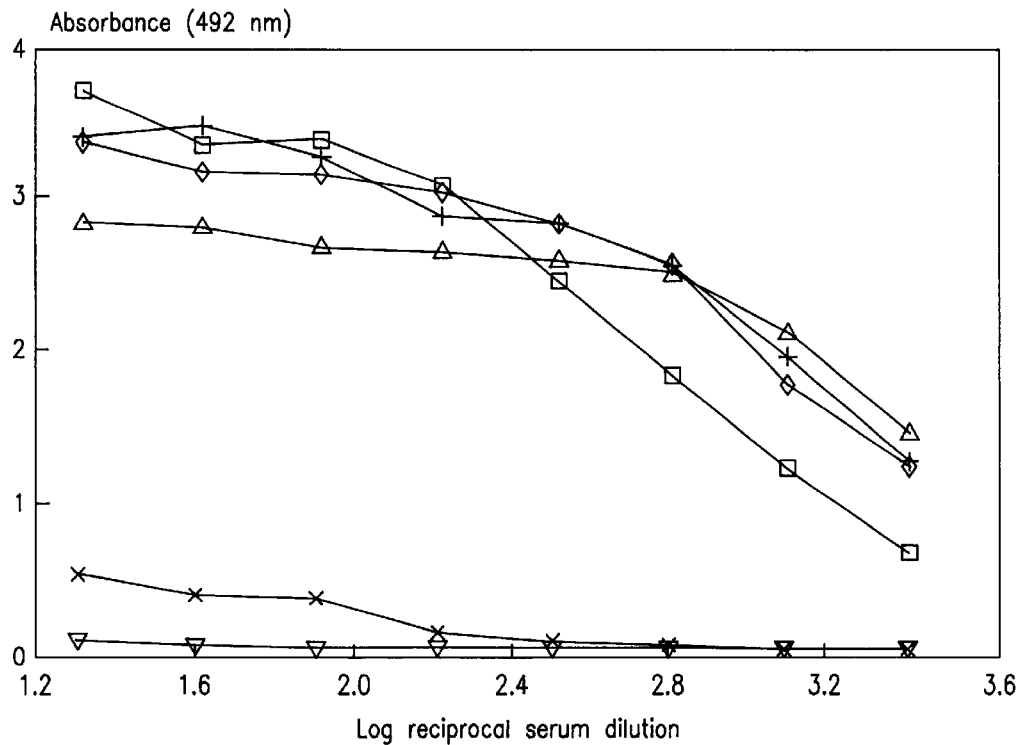
FIG. 2 shows the results of ELISA of retro-inverso model (mod) peptide-KLH antiserum against different immobilized peptide-BSA.—noMod (□), riMod (+), reMod (◊), inMod (Δ), control 1 (x), control 2 (∇).

It was found that all four antigens, including the D-amino acid-containing ones, were immunogenic. The antisera exhibited very similar antibody levels when assayed against approximately equal amounts of immobilised BSA conjugates of their respective peptide antigens. Furthermore, antibodies in each of the antisera also bound to the other three peptide antigens. The results of one such assay, where binding of the retro-inverso peptide-KLH antiserum to all four peptides was measured, is shown in FIG. 2. The fact that not only cross-reaction of noMod and riMod antibodies was observed, but also of antibodies against the non-isosteric antigens, was particularly surprising. This would indicate that the antibodies studied recognize amino acid side chain groupings in the antigen without any regard to the sequence direction and absolute configuration of the α-carbon atoms. Furthermore, the presence of proline residues in the peptide sequences did not prevent the D-amino acid-containing peptides from successfully mimicking the native sequence, as has been observed in retro-inverso peptide hormone analogues.

In order to account for the antibodies specific for the carrier protein attachment site -Gly-Cys-Gly-, i.e. the portion common to all antigens, an antiserum against a KLH conjugate of a 14-residue peptide with completely unrelated sequence, but containing the same attachment site, was also assayed (control 1 in FIG. 2). As can be seen, antibodies to this site do not appear to contribute significantly to the observed cross-reactivity (control 2 refers to observed binding of the riMod-KLH antiserum to BSA only)

Oral Immunization

Oral immunization with the free, i.e. non-conjugated, native and retro-inverso model peptides was carried out as follows: 0.3 mg/dose of the peptides in 50 mL PBS was administered to groups of mice according to the schedule outlined above for the i.p. immunization. The results of the ELISA of the resulting sera are summarised in Table 1. Results from the corresponding immunizations by injection are included for the purpose of comparison.

TABLE 1

ELISA of model peptide antisera

| Immobilized Material | Administration route | Antiserum | Days after last booster | Titre[a] |
|---|---|---|---|---|
| riMod-BSA | i.p. | riMod-KLH | 6 | >5,000 |
| riMod-BSA | i.p. | noMod-KLH | 6 | >5,000 |
| riMod-BSA |  | non- immune |  | 80 |
| riMod-BSA | i.p. | control[b] | 6 | 64 |
| BSA only | i.p. | riMod-KLH | 6 | 120 |
| riMod-BSA | oral | riMod | 6 | 512 |
| riMod-BSA | oral | riMod | 13 | 2,048 |
| riMod-BSA | oral | riMod | 26 | 2,048 |
| riMod-BSA | oral | riMod | 40 | 1,024 |
| noMod-BSA | i.p. | noMod-KLH | 6 | >5,000 |
| noMod-BSA | i.p. | riMod-KLH | 6 | >5,000 |
| noMod-BSA |  | non-immune |  | 80 |
| BSA only | i.p. | noMod-KLH | 6 | 64 |
| noMod-BSA | oral | riMod | 13 | 2,048 |
| noMod-BSA | oral | noMod | 6 | 0 |
| noMod-BSA | oral | noMod | 13 | 0 |

[a]Reciprocal of highest serum dilution giving statistically significant signal.
[b]Control peptide of 14 residues with unrelated sequence, apart from -Gly-Cys-Gly- protein conjugation site.

Oral immunization only gave a detectable serum IgG response in the case of the retro-inverso peptide. Again antibodies in the retro-inverso antiserum appeared to cross-react fully with the native peptide. Evidently the retro-inverso peptide, in contrast to the native peptide was capable of entering the circulation in a sufficient quantity to mount an IgG response. That the retro-inverso peptide is only slowly degraded is also indicated by the fact that anti-peptide IgG persisted in the blood stream of the animals for many weeks.

Example 6 a) Analysis of Antibody Production and Activity of Antibodies Raised to Peptide Sequences Corresponding to the Immunodominant Epitope of the Circumsporozoite Coat Protein of *P. falciparum* Sporozoites The following four peptides, based on the immunodominant epitope of the circumsporozoite coat protein of *P. falciparum* sporozoites, were synthesized:

noMalCys: H-Cys-Asn-Ala-Asn-Pro-Asn-Ala-Asn-Pro-Asn-Ala-Asn-Pro-OH (SEQ ID No.3)

noMal: H-Asn-Ala-Asn-Pro-Asn-Ala-Asn-Pro-Asn-Ala-Asn-Pro-OH (SEQ ID No.4)

riMalCys: H-pro-asn-ala-asn-pro-asn-ala-asn-pro-asn-ala-asn-Cys-OH riMal: H-pro-asn-ala-asn-pro-asn-ala-asn-pro-asn-ala-asn-OH The cysteine derivatives were protected as trityl thioethers for synthesis. Sequence-internal asparagines were coupled without side-chain protection as pentafluorophenyl esters. The deprotection of Fmoc-Asn-Pro-peptidyl resins was shortened to 3 min, followed by three 15 sec DMF washes and immediate acylation with Fmoc-Ala-OH/BOP-HOBt, in order to minimize loss (ca. 50%) of peptide due to diketopiperazine formation. Asparagine was coupled to synthesis resin as the Fmoc-Asn(Mbh)-OH symmetrical anhydride derivative Cleavage/deprotection was achieved with 5% thiophenol in TFA for the noMalCys- and riMalCys-peptidyl resins and with 5% aqueous TFA for the noMal- and riMal-resins. After cleavage, the crude riMal peptide was further treated for 2 h at room temperature with 5% thioanisole in TFA to remove completely the dimethoxybenzhydryl protecting group.

Groups of mice were immunized i.p. at weekly intervals for a total of four weeks with 100 μg doses of noMalCys- and riMalCys-KLH conjugates. Blood was collected after five weeks and the serum titres established by ELISA (Table 2).

TABLE 2

ELISA of antisera to malaria peptide-KLH conjugates

| Immobilized antigen | Antiserum to | Titre[a] |
|---|---|---|
| noMalCys-BSA | noMalCys-KLH | >12,000 |
| noMalCys-BSA | riMalCys-KLH | 1,500 |
| riMalCys-BSA | noMalCys-KLH | >12,000 |
| riMalCys-BSA | riMalCys-KLH | 3,000 |

[a]Reciprocal of highest serum dilution showing significant above background reading (average over four individual sera).

Figure 3:
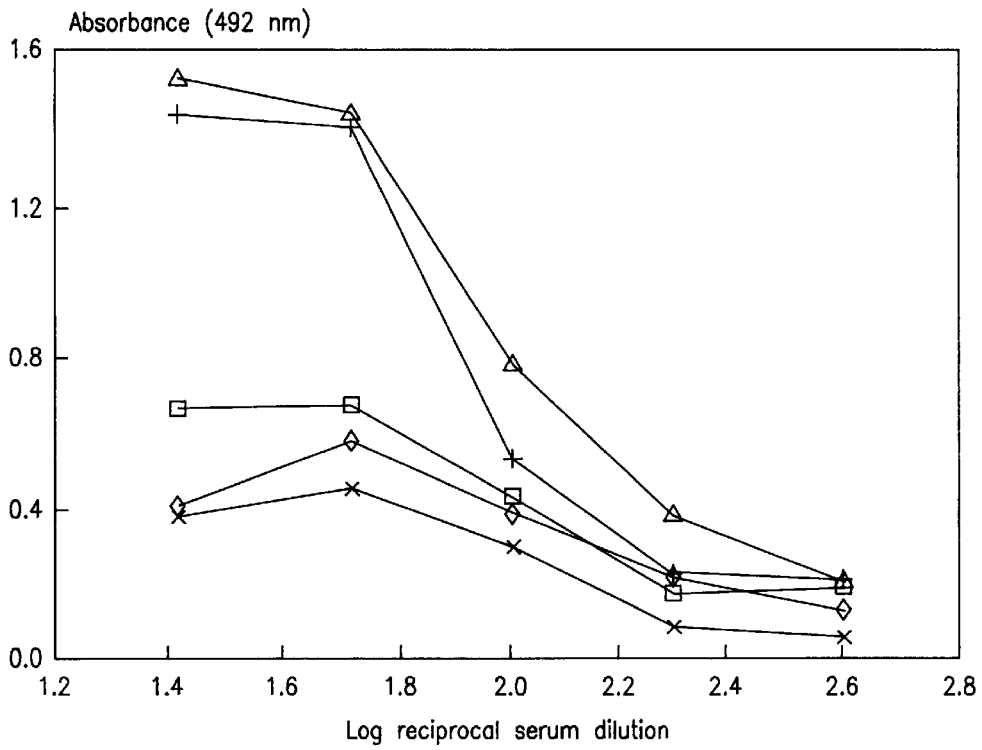
FIG. 3 shows the results of ELISA of malaria (Mal)-peptide antisera (oral immunization) against peptide-BSA.—Serum/immobilized antigen: riMal/riMal (Δ), riMal/noMal (+) , noMal/noMal (□), noMal/riMal (◊), non-immune serum/noMal (X)
Figure 4:
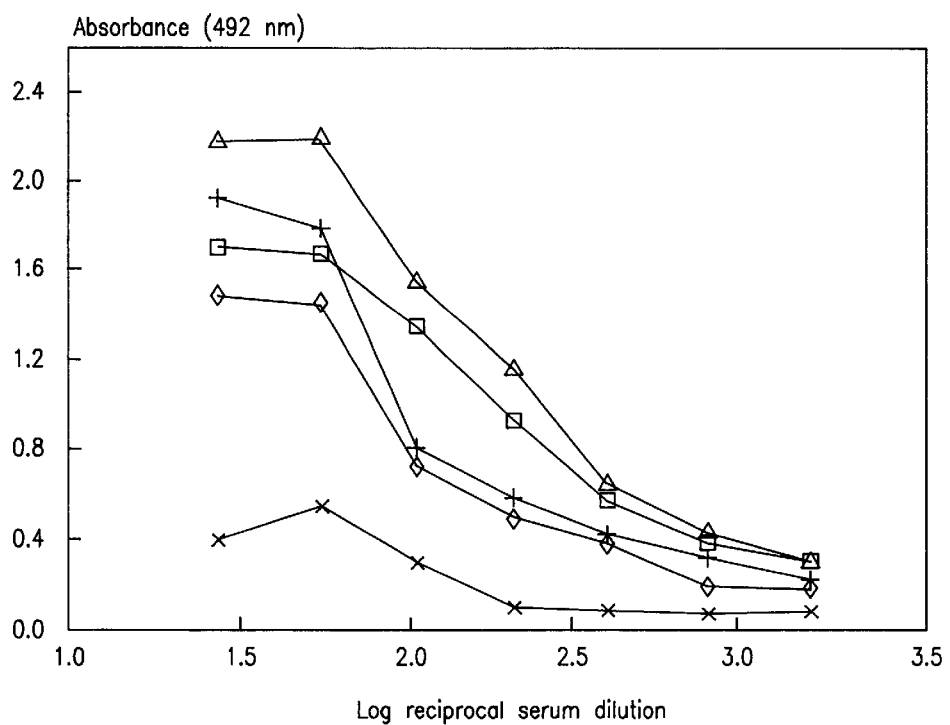
FIG. 4 shows the results of ELISA of diphtheria (DIP) peptide-KLH antisera against immobilized peptide-BSA.—Serum/immobilized antigen: riDip/riDip (Δ), riDip/noDip (+), noDip/noDip (□), noDip/riDip (◊), non-immune/noDip (x).
Figure 5:
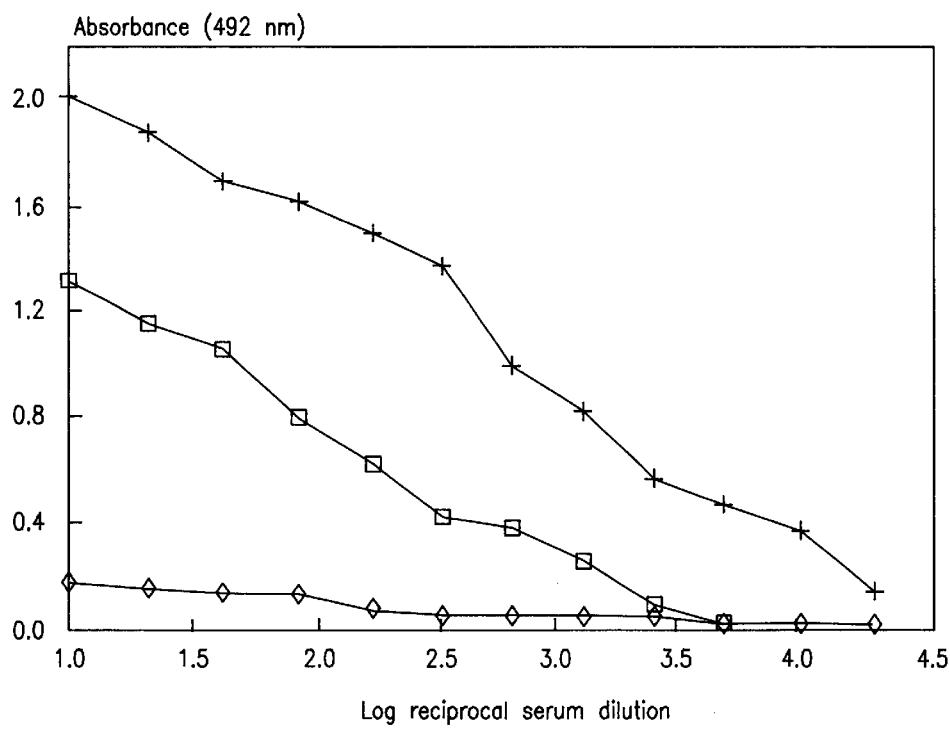
FIG. 5 shows the results of ELISA of diphtheria (Dip) peptide-KLH antisera against immobilized diphtheria toxin.—Anti-riDip (+), anti-noDip (□), non-immune serum (◊).
Figure 6:
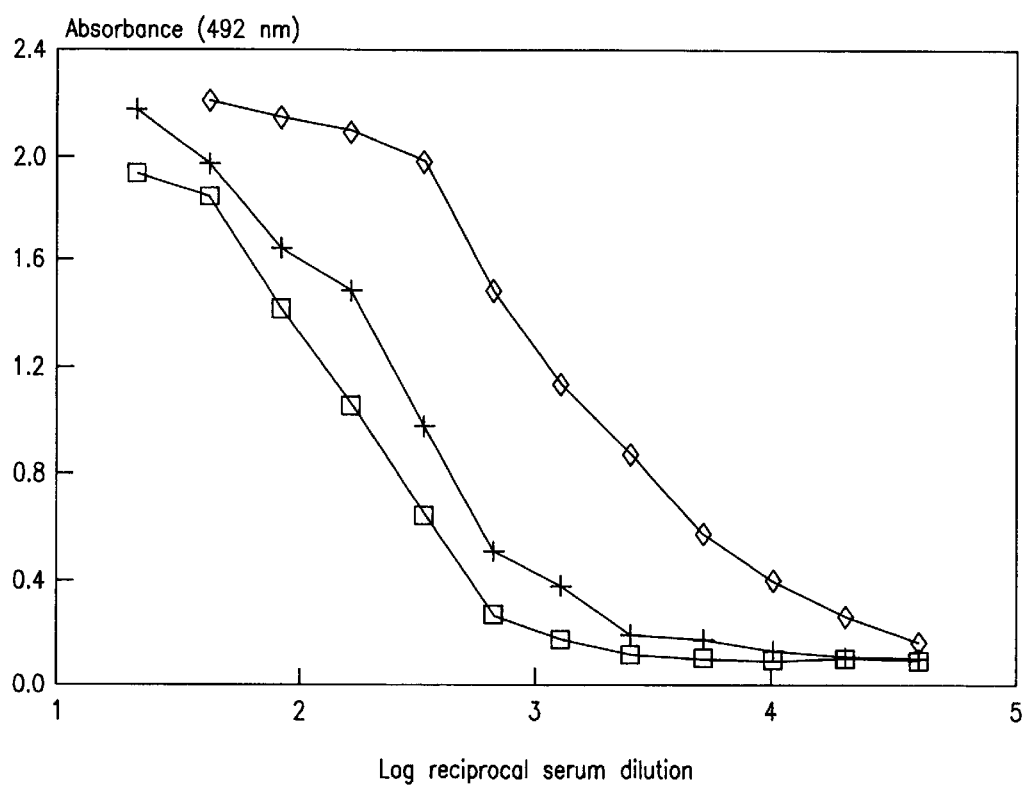
FIG. 6 shows the results of ELISA of orally induced diphtheria (Dip) peptide antisera against immobilized diphtheria toxin.—Anti-noDip, 2 weeks (□); anti-riDip, 2 weeks (+) anti-riDip, 8 weeks (◇).

Here the native antigen was found to be more immunogenic than the retro-inverso antigen. As in the previous examples, the antisera were fully cross-reactive. Mice were immunized orally with the noMal and riMal peptides at weekly intervals for a total of four weeks. Blood was collected and assayed by ELISA after five weeks. The results of the titration are shown in FIG. 3. Only the retro-inverso peptide induced a significant titer of anti-peptide antibodies. There appeared to be full cross-reactivity of these antibodies with the normal peptide, in the same way as the peptide-KLH antisera were fully cross-reactive.

b) Testing of no/riMal Peptides with Sera from Malaria Patients

It has been shown that high levels of antibodies directed against circumsporozoite protein repeat sequences can inhibit sporozoite development (Mazier et al., 1986). Furthermore, a recombinant vaccine containing such repeats, as well as a peptide vaccine consisting of three NANP repeats coupled to tetanus toxoid, have shown some promise in clinical trials (Herrington et al., 1987 & 1990). After having demonstrated that antisera raised in animals against the noMal and riMal peptides were cross-reactive, it was important to show that anti-sporozoite antibodies in humans with malaria recognized both peptides.

Serum samples from Thai malaria patients were obtained. These sera were known to contain antibodies against the immunodominant epitope of the *Plasmodium falciparum* circumsporozoite protein (Wirtz et al., 1989). With a few exceptions, all the patients had clinically diagnosed malaria and had suffered attacks recently.

We tested these sera for antibodies capable of binding to a recombinant circumsporozoite construct, a synthetic polymer and noMal, all of which contain NANP repeats, as well as riMal. The results are summarized in Table 3. As can be seen, for most sera there is good correlation of the results, the binding to those antigens containing a large number of NANP repeats being stronger. In every case cross-reaction of the antisera between the normal and retro-inverso forms of the (NANP)$_3$ peptide was observed.

Table 3

IgG Antibodies in Human Sera from Malaria Sufferers Recognize noMal and riMal Peptides Coated ELISA plates were incubated with serially diluted human sera. The plates were then washed and bound antibodies detected using anti-human IgG coupled to horseradish peroxidase. The results were expressed on a scale where + signifies a titer (highest serum dilution giving a significant signal) of 1/320 to +++++ which indicates a titre >2,560. All results were corrected for non-specific binding by using two non-related peptides, conjugated to BSA in the same way as noMal and riMal, as controls.

| Serum | Immobilized antigen[a] | | | |
|---|---|---|---|---|
| | (NANP)[b]$_{50}$ | Falc 2.3 CS[c] | noMal-BSA | riMal-BSA |
| 014 | +++ | ++++ | +++ | +++ |
| 015 | ++ | ++ | ++ | + |
| 016 | +++ | +++ | +++ | ++ |
| 021 | + | ++ | + | + |
| 022 | ++++ | +++++ | + | ++ |
| 034 | ++ | +++ | + | + |
| 048 | + | +++ | + | + |
| 054 | +++ | ++++ | +++ | ++ |
| 055 | ++++ | +++ | +++ | +++ |
| 061 | ++ | ++++ | + | ++ |
| 063 | +++ | +++ | + | ++ |
| 067 | ++ | +++ | + | ++ |
| 119 | ++++ | +++++ | ++++ | +++ |
| 121 | ++ | +++ | + | + |
| 122 | +++ | +++++ | ++ | +++ |
| 134 | +++ | ++++ | + | ++ |
| 136 | +++ | ++++ | ++ | ++ |

[a]ELISA microtitre plates were coated with 10 µg/well of the appropriate antigen
[b]A synthetic polymer, i.e. approximately 50 repeats of the Asn-Ala-Asn-Pro sequence, prepared according to Etlinger et al. (1988).
[c]A recombinant protein expressed in yeast (Barr et al., 1987) and containing residues 43–391 (Dame et al., 1984) of the *P. falciparum* circumsporozoite protein.

Example 7

Figure 7:
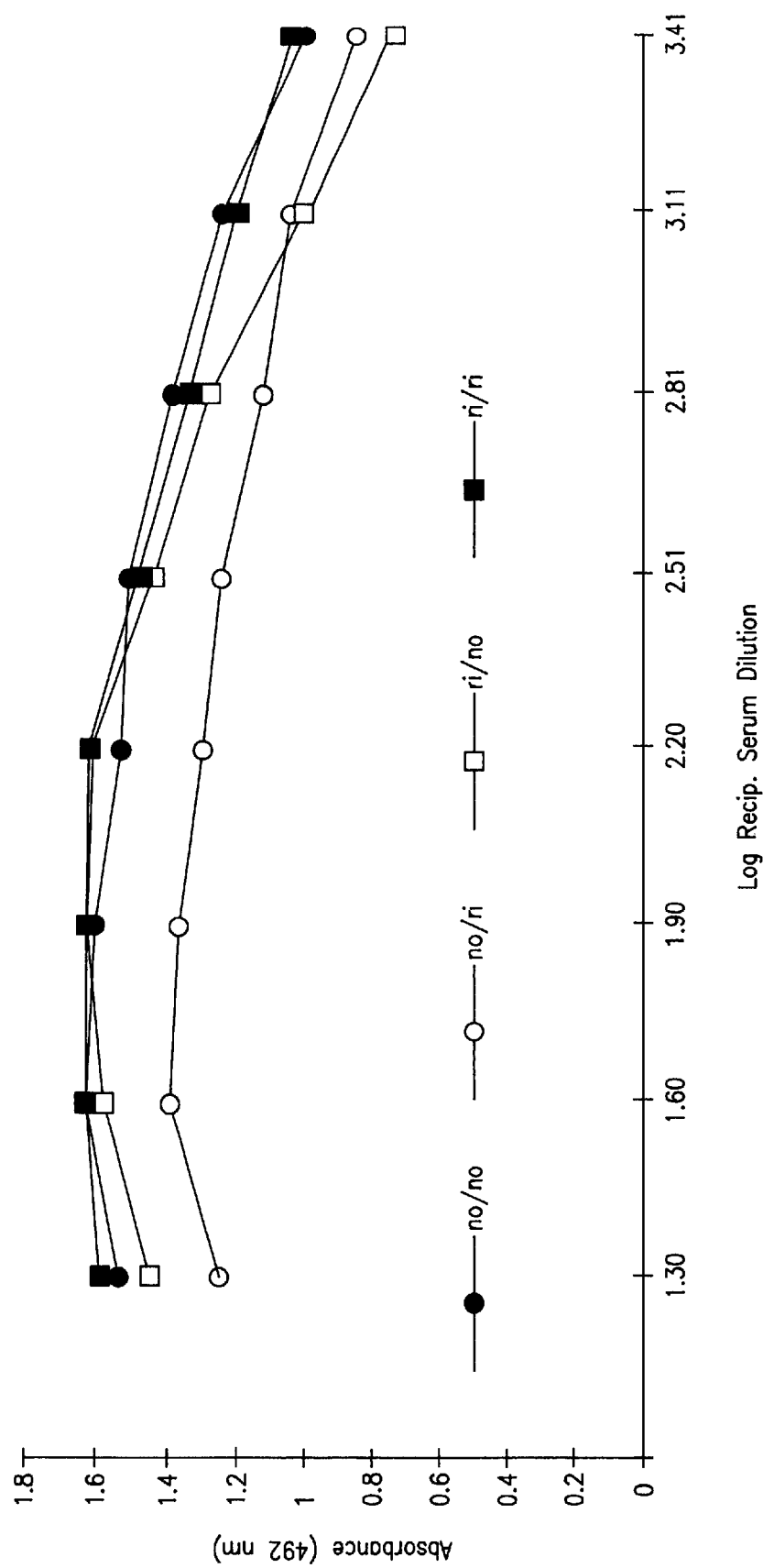
FIG. 7 shows the results of ELISA of HIVgp41(735–753) antisera against immobilized peptide: serum/immobilized antigen.
Figure 8:
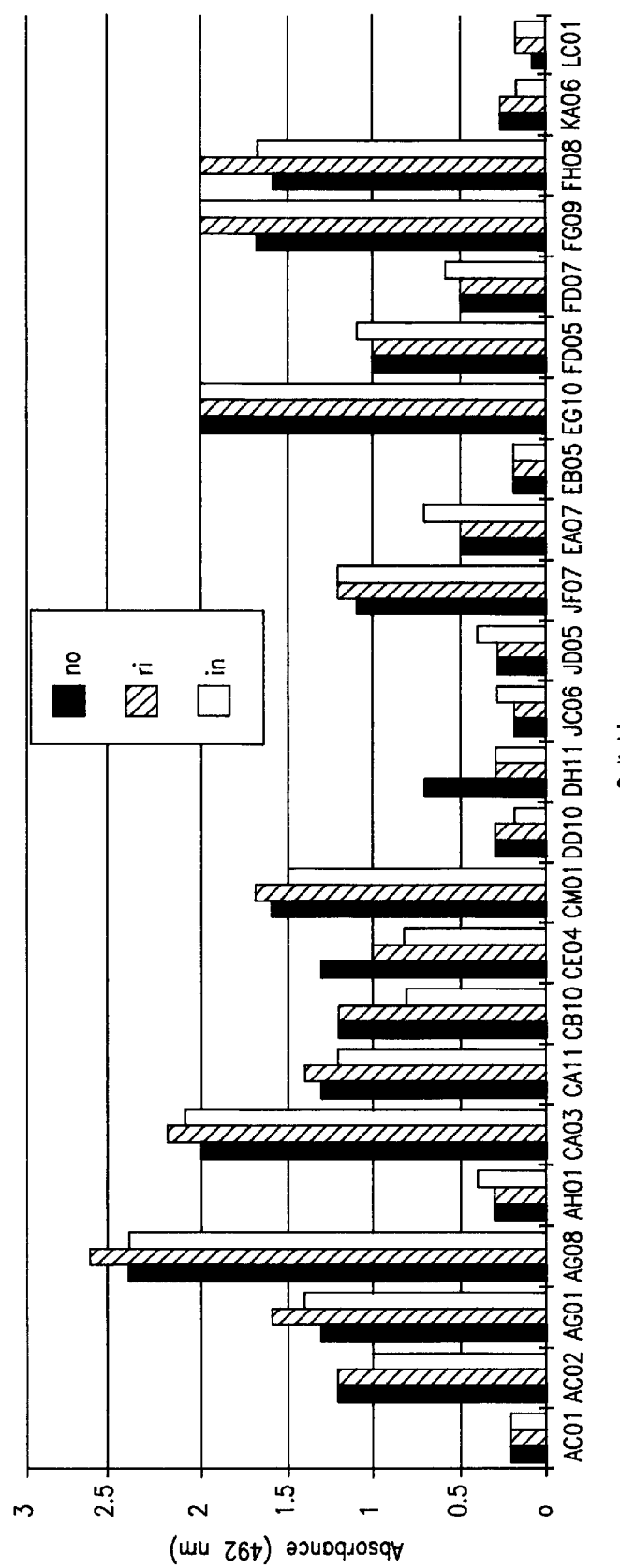
FIG. 8 shows the results of ELISA of HIVgp41 monoclonals with gp41 peptides.

Analysis of Antibody Production and Activity of Antibodies Raised to Peptide Sequences Corresponding to the Amino Acid Sequence of Diphtheria Toxin The following two peptides, based on the loop sequence of the 14 amino acid residues subtended by the disulphide bridge near the amino-terminus of the diphtheria toxin molecule, were synthesized:

noDip: H-Gly-Asn-Arg-Val-Arg-Arg-Ser-Val-Gly-Ser-Ser-Leu-Lys-Cys-OH (SEQ ID No.5)

riDip: H-cys-lys-leu-ser-ser-Gly-val-ser-arg-arg-val-arg-asn-Gly-OH

The side-chain protecting groups used were: trityl for cysteine, t-butoxycarbonyl for lysine, t-butyl for serine and 4-methoxy-2,3,6-trimethylbenzenesulphonyl for arginine. Asparagine was coupled as the free side-chain amide and in the form of the pentafluorophenyl ester (Gausepohl et al., 1989) in both cases. Cleavage and side-chain deprotection were accomplished by reaction of the peptidyl resins for 75 min at 0° C. with 1M trimethylsilyl bromide-thioanisole in TFA containing 0.25M 1,2-ethanedithiol (Yajima et al., 1988).

Mice (4 per antigen) were immunized i.p. with 100 μg doses of KLH-conjugated normal and retro-inverso peptide on day 0, followed by boosters on days 4, 9 and 16. Blood was collected on day 21 and the sera pooled. IgG antibodies against the peptides were measured using an ELISA with immobilised BSA-peptide conjugates. The results are summarized in FIG. 4. Both the normal and the retro-inverso peptide-KLH conjugates produced similar titers of antibodies, again showing that the presence of unnatural amino acids in the antigen leads to retention of immunogenicity. Furthermore, the results show that IgG in both antisera recognize both antigens equally well.

The antisera were further assayed for their capacity to recognize their antigen sequence in diphtheria toxin itself. An ELISA with immobilised diphtheria toxin (1 μg/well) was used for this purpose. The results in FIG. 5 demonstrate that IgG antibodies in both antisera bound to the toxin. The retro-inverso-peptide-KLH antiserum exhibited a very high antitoxin titre (ca. ten times higher than the titer of the normal antiserum).

A further surprising result was recorded upon oral immunization with the free native and retro-inverso diphtheria peptides. Here mice were given a single dose of ca. 1 mg peptide. After one and two weeks, serum samples from animals immunized with either peptide contained antibodies which bound to diphtheria toxin. In both cases the anti-toxin titre was considerable. Eight weeks after immunization, on the other hand, only the animals having received the retro-inverso peptide appeared to contain anti-toxin antibodies (FIG. 6). Furthermore, the titre measured was very high and comparable to that obtained by boosted i.p. immunization with the corresponding KLH-conjugate.

Example 8

HIV-1 Peptides

Many AIDS vaccines consisting of recombinant viral proteins or synthetic peptides have been proposed and are being tested (Spalding, 1992). A variety of epitopes, mostly from the virus coat glycoproteins gp120 and gp41, have been associated with the ability to induce virus-neutralizing antibodies. For our studies we chose the gp41 sequences 735–753 (Chanh et al., 1986) and 583–599 (Klasse et al., 1988) and the following peptides were prepared:

noHIVgp41(735–753) H-Tyr-Asp-Arg-Pro-Glu-Gly-Ile-Glu-Glu-Glu-Gly-Gly-Glu-Ara-Asp-Arg-Asp-Arg-Ser-$NH_2$ (SEQ ID No.6)

riHIVgp41(735–753) H-ser-arg-asp-arg-asp-arg-glu-Gly-Gly-glu-glu-glu-ile-Gly-glu-pro-arg-asp-tyr-$NH_2$ noHIVgp41(583–599) H-Leu-Gln-Ala-Arg-Ile-Leu-Ala-Val-Glu-Arg-Tyr-Leu-Lys-Asp-Gln-Gln-Leu-$NH_2$ (SEQ ID No.7)

inHIVgp41(583–599) H-leu-gln-ala-arg-ile-leu-ala-val-glu-arg-tyr-leu-lys-asp-gln-gln-leu-$NH_2$ riHIVgp41(583–599) H-leu-gln-gln-asp-lys-leu-tyr-arg-glu-val-ala-leu-ile-arg-ala-gln-leu-$NH_2$ The syntheses were carried out as usual but using synthesis resin with trialkoxydiphenyl-amide linkage (Rink, 1987). Conjugates with BSA and KLH were prepared by glutaraldehyde polymerization according to Mariani et al. (1987). Groups of mice were immunized with 100 μg/dose of the HIVgp41(735–753) peptide-KLH conjugates in Freund's complete adjuvant, followed by two booster injections with Freund's incomplete adjuvant at fortnightly intervals. Blood was collected two weeks after the last booster and sera were prepared.

Murine monoclonal hybridoma cell lines producing antibodies against HIV-1gp41 protein were obtained by immunization with recombinant gp41. The spleen cells of the animal with the best immune response were isolated and fused with NS-1 myeloma cells using polyethylene glycol-4,000. The resulting cells were plated out and submitted to limiting dilution cloning.

Polyclonal antisera against both the HIVgp41(735–753) peptides were analyzed by ELISA. The results are shown in FIG. 7. ELISA plates were coated with noHIVgp41 (735–753)-BSA and riHIVgp41(735–753)-BSA at S μg/well for 1 h in carbonate buffer, pH 9.6. After 1 h, the plates were blocked with boiled casein solution. They were then incubated for 1 h with serially diluted sera from mice immunized with the peptide-KLH conjugates. A goat-anti-mouse IgG antibody labelled with horseradish peroxidase was used for detection. The results were corrected for non-specific binding (determined using unrelated peptide-BSA conjugates). The averages of five data points (corresponding to five individual mice per antigen group) are plotted. The data point labels (e.g. no/no) refer to coated antigen/antiserum. Clearly the extent of cross-reaction between the antibodies to the two forms of the peptide is high. In order to demonstrate that individual antibodies are capable of recognizing different forms of a peptide, ELISA experiments were carried out using monoclonal antibodies against gp41. The results with the HIVgp41(583–599) peptides are shown in FIG. 8. A library of cell lines producing antibodies against HIVgp41 was prescreened by ELISA using noHIVgp41 (583–599)-BSA immobilized on microtitre plates. Twenty four clones were further tested: 100 μL of cell supernatant was incubated with 5 μg/well of each of the three peptide-BSA conjugates. The plates were washed and bound antibodies detected with the aid of an anti-mouse IgG-horseradish peroxidase conjugate. The uncorrected color signals after development with o-phenylenediamine/peroxide are plotted, against the cell line designations. In every case where a monoclonal antibody recognized one form of the peptide, it also bound to the other two forms; indeed the extent of cross-reaction appeared to be complete. Some cell lines against gp41 which recognized the HIVgp41 (735–753) peptides were also identified, again cross-reaction was found.

Example 9

Retro-inverso Robustoxin (riRtx)

The potentially lethal robustoxin is found in the venom of the male funnel-web spider (Nicholson et al., 1991). It has been shown that immunization with a vaccine prepared from a synthetic analogue of this toxin can protect mice and monkeys from challenges with native toxin (Mylecharane et al., 1991). In order to demonstrate the utility of retro-inverso peptides as vaccines, a retro-inverso analogue of robustoxin, having the following sequence, was prepared:

H-cys(Acm)-lys-lys-phe-leu-Gly-thr-ile-thr-thr-glu-cys(Acm)-ser-Gly-gln-gln-asn-tyr-trp-ala-tyr-ile-cys(Acm)-lys-met-pro-cys(Acm)-cys(Acm)-cys(Acm)-asp-glu-asn-lys-Gly-cys(Acm)-trp-asn-arg-lys-lys-ala-cys(Acm)-OH The peptide was purified and its structure verified by gas-phase sequence analysis. The vaccine was prepared by polymerizing 0.2 mg of the peptide and 0.8 mg KLH in 1 mL of phosphate-buffered saline with 10 μL of 25 % aq. glutaraldehyde at room temperature overnight. The reaction was stopped by the addition of 100 μL of 2 % lysine solution.

Groups of mice were immunized with this material or with a vaccine prepared similarly but using normal Cys(Acm)-protected synthetic robustoxin according to the following schedule: fortnightly injections of 50 μg peptide-KLH, the first two subcutaneously and three more boosters intraperitoneally. These animals, as well as non-immunized controls, were then challenged 14 weeks after the last booster immunization with 2 minimal lethal doses (the lethal dose determination was carried out immediately prior to the challenge) of funnel-web spider venom by intravenous injection. The non-immunized animals succumbed within ten minutes, whereas those immunized with the native vaccine survived. Of the ri-Rtx-KLH immunized individuals, one expired after 24 h while the remaining seven survived the challenge.

Example 10

Hepatitis C Virus Envelope Peptide

The following two peptides, based on the envelope sequence (306–330) of the hepatitis C virus, were synthesized.

noCEnv H-Cys-Ser-Ile-Tyr-Pro-Gly-His-Ile-Thr-Gly-His-Arg-Met-Ala-Trp-Asp-Met-Met-Met-Asn-Trp-Ser-Pro-Thr-Ala-OH (SEQ ID No.8)

riCEnv H-ala-thr-pro-ser-trp-asn-met-met-met-asp-trp-ala-met-arg-his- Gly-thr-ile-his-Gly-pro-tyr-ile-ser-cys-$NH_2$ The synthesis of noCEnv was carried out on polyamide PepsynKA resin pre-esterified with Fmoc-Ala and riCEnv was on Polyhipe Rink resin. The side chain protecting groups used were: trityl for cysteine, histidine and asparagine, t-butyl for serine, threonine and aspartic acid and 2,2,5,7,8-pentamethyl chroman-6-sulphonyl for arginine. Cleavage and side-chain deprotection were accomplished by reaction of the peptidyl resins for 90 min at 0° C. with 1M trimethylsilylbromide-thioanisole in TFA containing 0.25M 1,2-ethanedithiol (Yajima et al., 1988). The peptides were conjugated to BSA as described in Example 2.

Both peptides were tested in ELISA using the method described in Example 11 against sera from HCV positive patients in China. NoCEnv detected 15/30 (50%) of positive sera tested and riCEnv gave similar results.

Example 11

Hepatitis C Capsid Peptide

The following two peptides, based on the capsid sequence (39–74) of the hepatitis C virus, were synthesized.

noCCap H-Cys-Arg-Arg-Gly-Pro-Arg-Leu-Gly-Val-Arg-Ala-Thr-Arg-Lys-Thr-Ser-Glu-Arg-Ser-Gln-Pro-Arg-Gly-Arg-Arg-Gln-Pro-Ile-Pro-Lys-Val-Arg-Arg-Pro-Glu-Gly-Arg-OH (SEQ ID No.9)

riCCap H-Cys-arg-Gly-glu-pro-arg-arg-val-lys-pro-ile-pro-gln-arg-arg-Gly-arg-pro-gln-ser-arg-glu-ser-thr-lys-arg-thr-ala-arg-val-Gly-leu-arg-pro-Gly-arg-arg-$NH_2$ The synthesis of noCCap was carried out on polyamide PepsynKA resin pre-esterified with Fmoc-Arg(Mtr) and riCCap was on Polyhipe Rink resin. The side chain protecting groups used were: trityl for cysteine and glutamine, t-butyl for serine, threonine and glutamic acid, t-butoxycarbonyl for lysine and 2,2,5,7,8-pentamethyl chroman-6-sulphonyl for arginine. Cleavage and side-chain deprotection were accomplished by reaction of the peptidyl resins for 90 min at 0° C. with 1M trimethylsilylbromide-thioanisole in TFA containing 0.25M 1,2-ethanedithiol (Yajima et al., 1988). The peptides were conjugated to BSA as described in Example 2.

The wells of PVC microtitre plates were coated with the appropriate antigen (0.05–1 μg/well) dissolved in dilute carbonate/bicarbonate buffer pH9.6 and incubated overnight at 4° C. After aspiration, blocking was effected by incubation for 1 h at 37° C. with carbonate/bicarbonate buffer pH9.6 containing 20% calf serum. The wells were then washed four times with 0.2% Tween 20 in PBS before addition of antiserum, serially diluted in double strength PBS containing 0.5% BSA, 10% calf serum and 0.2% Triton X 100 (antibody binding buffer). After incubation for 1 h at 37° C., the plates were again washed Bound IgG was detected by incubation for 30 min at 37° C. with suitably diluted affinity purified anti-human IgG horse radish peroxidase in antibody binding buffer. After washing, the plates were developed with 3,3'5,5' tetramethylbenzidine (TMB), 0.01; peroxide at pH5 in the dark. Color development was stopped by the addition of 2M sulphuric acid and the plates were read at wavelengths of 450 nm/630 nm.

The BSA conjugated peptides noCCap and riCCap were coated on ELISA plates and tested against sera from Chinese hepatitis C patients. The results are summarized in the table below. In each case cross-reaction between normal and retro-inverso forms of the capsid peptide was observed and with serum No. 1 the retro-inverso peptide gave higher titers than the normal peptide.

|  |  | Serum Dilution | | | | | | | | | |
|---|---|---|---|---|---|---|---|---|---|---|---|
|  |  | Positive Serum | | | | | | | | | Negative |
| Peptide |  | No. 1 | | | No. 2 | | | No. 3 | | | Control |
| ng/well | Blank | 1:10 | 1:25 | 1:50 | 1:10 | 1:25 | 1:50 | 1:10 | 1:25 | 1:50 | 1:50 |
| noCCap (100 ng) | 0.019 | 0.473 | 0.227 | 0.152 | 1.257 | 0.456 | 0.244 | 2.085 | 1.884 | 1.203 | 0.058 |
| riCCap (100 ng) | 0.021 | 0.963 | 0.491 | 0.338 | 1.130 | 0.779 | 0.544 | 1.719 | 1.651 | 1.238 | 0.122 |
| noCCap (50 ng) | 0.018 | 0.534 | 0.255 | 0.175 | 1.817 | 0.772 | 0.488 | 2.036 | 2.008 | 1.416 | 0.060 |
| riCCap (50 ng) | 0.017 | 0.930 | 0.547 | 0.361 | 1.146 | 0.663 | 0.505 | 1.643 | 1.550 | 1.166 | 0.135 |

Example 12

HIV Diagnostic Peptides

Peptides from the Envelope Protein of the Human Immunodeficiency Virus

The following two peptides, based on residues 579–611 of the envelope protein of the human immunodeficiency virus, were synthesized.

noHIVgp41(579–611) H-Arg-Ile-Leu-Ala-Val-Glu-Arg-Tyr-Leu-Lys-Asp-Gln-Gln-Leu-Leu-Gly-Ile-Trp-Gly-Aba-Ser-Gly-Lys-Leu-Ile-Aba-Thr-Thr-Ala-Val-Pro-Trp-Asn-Cys-OH (SEQ ID No.10)

riHIVgp41(579–611) H-Cys-asn-trp-pro-val-ala-thr-thr-cys(acm)ile-leu-lys-Gly-ser-cys(Acm)Gly-trp-ile-Gly-leu-leu-gln-gln-asp-lys-leu-tyr-arg-glu-val-ala-leu-ile-arg-NH$_2$ The synthesis of noHIVgp41(579–611) was carried out on polyamide PepsynKA resin pre-esterified with Fmoc-Cys (trt) and riHIVgp41(579–611) was on Polyhipe Rink resin. The side chain protecting groups used were: trityl for terminal cysteine, glutamine and asparagine, t-butyl for serine, threonine, aspartic acid, glutamic acid and tyrosine, t-butoxycarbonyl for lysine and 2,2,5,7,8-pentamethyl chroman-6-sulphonyl for arginine. Cysteine was replaced by aminobutyric acid (Aba) in noHIVgp41(579–611) and by cysteine with acetamidomethyl (Acm) protection of the sulfhydryl group in riHIVgp41(579–611). Cleavage and side-chain deprotection were accomplished by reaction of the peptidyl resins for 90 min at 0° C. with 1M trimethylsilylbromide-thioanisole in TFA containing 0.25M 1,2-ethanedithiol (Yajima et al., 1988). The acetamidomethyl (Acm) protection of cysteine was not removed by this procedure. The peptides were conjugated to BSA as described in Example 2.

Example 13

Peptides from gp41 of the Human Immunodeficiency Virus

The following two peptides, based on the gp41 protein sequence 735–752 of the human immunodeficiency virus, were synthesized.

noHIVgp41 (735–753) H-Tyr-Asp-Arg-Pro-Glu-Gly-Ile-Glu-Glu-Glu-Gly-Gly-Glu-Arg-Asp-Arg-Asp-Arg-Ser-NH$_2$ (SEQ ID No.6)

riHIVgp41 (735–753) H-ser-arg-asp-arg-asp-arg-glu-Gly-Gly-glu-glu-glu-ile-Gly-glu-pro-arg-asp-tyr-NH$_2$ The synthesis of both peptides was carried out on Polyhipe Rink resin. The side chain protecting groups used were: t-butyl for serine, aspartic acid, glutamic acid and tyrosine, and 2,2,5,7,8-pentamethyl chroman-6-sulphonyl for arginine. Cleavage and side-chain deprotection were accomplished by reaction of the peptidyl resins for 90 min at 0° C. with 1M trimethylsilylbromide-thioanisole in TFA containing 0.25M 1,2-ethanedithiol (Yajima et al., 1988). A sulfhydryl group was introduced at the N-terminus of these peptides by reaction with 2-iminothiolane.HCl (Traut's Reagent). (Jue, R. et al., 1978). The peptides were conjugated to BSA as described in Example 2.

The wells of PVC microtitre plates were coated with the appropriate antigen (0.05–1 μg/well) dissolved in dilute carbonate/bicarbonate buffer pH9.6 and incubated overnight at 4° C. After aspiration, blocking was effected by incubation for 1 h at 37° C. with carbonate/bicarbonate buffer pH9.6 containing 20% calf serum. The wells were then washed four times with 0.2% Tween 20 in PBS before addition of antiserum, serially diluted in double strength PBS containing 0.5% BSA, 10% calf serum and 0.2% Triton X 100 (antibody binding buffer). After incubation for 1 h at 37° C., the plates were again washed. Bound IgG was detected by incubation for 30 min at 37° C. with suitably diluted affinity purified anti-human IgG horse radish peroxidase in antibody binding buffer. After washing, the plates were developed with 3,3'5,5' tetramethylbenzidine (TMB), 0.01% peroxide at pH5 in the dark. Color development was stopped by the addition of 2M sulphuric acid and the plates were read at wavelengths of 450 nm/630 nm.

The BSA conjugated peptides noHIVgp41(579–611), riHIVgp41(579–611) from Example 12 and noHIVgp41 (735–753) and riHIVgp41(735–753) from this Example were coated on ELISA plates and tested in China against sera from patients with HIV positive sera. The results are summarized in the table below. In each case cross-reaction between normal and retro-inverso forms of the gp41 peptide was observed.

| | | Serum Dilution | | | | | | | | |
|---|---|---|---|---|---|---|---|---|---|---|
| | | Positive Serum | | | | | | | | Negative |
| Peptide | | No. 1 | | | No. 2 | | | No. 3 | | Control |
| ng/well | Blank | 1:10 | 1:25 | 1:50 | 1:10 | 1:25 | 1:50 | 1:10 | 1:25 | 1:50 | 1:50 |
| noHIVgp41 (735–753) (200 ng) | 0.023 | 0.497 | 0.242 | 0.139 | 0.506 | 0.266 | 0.153 | 0.275 | 0.151 | 0.099 | 0.153 |
| riHIVgp41 (735–753) (200 ng) | 0.025 | 0.477 | 0.219 | 0.135 | 0.527 | 0.271 | 0.570 | 0.262 | 0.155 | 0.090 | 0.132 |
| noHIVgp41 (579–611) (200 ng) | 0.022 | 0.483 | 0.210 | 0.133 | 0.617 | 0.339 | 0.205 | 0.278 | 0.182 | 0.115 | 0.148 |
| riHIVgp41 (579–611) (200 ng) | 0.018 | 0.453 | 0.231 | 0.150 | 0.660 | 0.339 | 0.194 | 0.241 | 0.140 | 0.087 | 0.155 |

Example 14

Analysis of Antibody Production and Activity of Antibodies Raised to Peptide Sequences Corresponding to Residues 126–137 of the Surface Protein of the Hepatitis B Virus The following two peptides, based on residues 126–137 of the surface protein of the Hepatitis B virus, were synthesized.

noHBV-S(126–137) H-Cys-Lys-Thr-Thr-Pro-Ala-Gln-Gly-Asn-Ser-Met-Tyr-Pro-Ser-OH (SEQ ID No.11)

riHBV-S(126–137) H-Lys-ser-pro-tyr-met-ser-asn-Gly-gln-ala-pro-thr-thr-Cys-OH

The synthesis of noHBV-S(126–137) was carried out on polyamide PepsynKA resin pre-esterified with Fmoc-Ser (tBu) and riHBV-S(126–137) was on polyamide PepsynKA resin pre-esterified with Fmoc-Cys(trt). Lysine was not part of the HBV sequence but was included to increase solubility. The side chain protecting groups used were: trityl for cysteine, glutamine and asparagine, t-butyl for serine, threonine and tyrosine and t-butoxycarbonyl for lysine. Cleavage and side-chain deprotection were accomplished by reaction of the peptidyl resins for 90 min at room temperature with 10 ml of TFA, 0.25 ml 1,2-ethanedithiol, 0.5 ml thioanisole, 0.5 ml water and 0.75 g phenol.

noHBV-S(126–137) was conjugated to KLH and both peptides were independently conjugated to BSA.

The KLH conjugate was emulsified in Freund's complete adjuvant (1:1) and used to immunize white Swiss mice according to the following schedule:

| Day 0: | 20 μg of peptide in 100 μl emulsion, subcutaneous (complete Freund's). |
|---|---|
| Day 10: | 20 μg of peptide in 100 μl emulsion, subcutaneous (incomplete Freund's). |
| Day 20: | 20 μg of peptide in 100 μl emulsion, intraperitoneally (incomplete Freund's). |

The mice (4 in each group) were bled retro-orbitally five days after the last injection and the serum used in ELISA using microtitre plates coated with 1 μg/well of the appropriate peptide conjugated to BSA.

| | O.D. 492 nm | |
|---|---|---|
| Plate coating: Antiserum to: | noHBV-S(126–137) noHBV | riHBV-S(126–137) noHBV |
| Dilution: | | |
| 1:50 | 2.551 | 3.057 |
| 1:100 | 2.673 | 2.946 |
| 1:200 | 2.317 | 2.876 |
| 1:400 | 2.161 | 2.355 |
| 1:800 | 2.039 | 1.746 |
| 1:1,600 | 1.540 | 1.081 |
| 1:3,200 | 0.965 | 0.673 |
| 1:6,400 | 0.619 | 0.481 |
| 1:12,800 | 0.506 | 0.340 |
| 1:25,600 | 0.299 | 0.244 |

Figure 9:
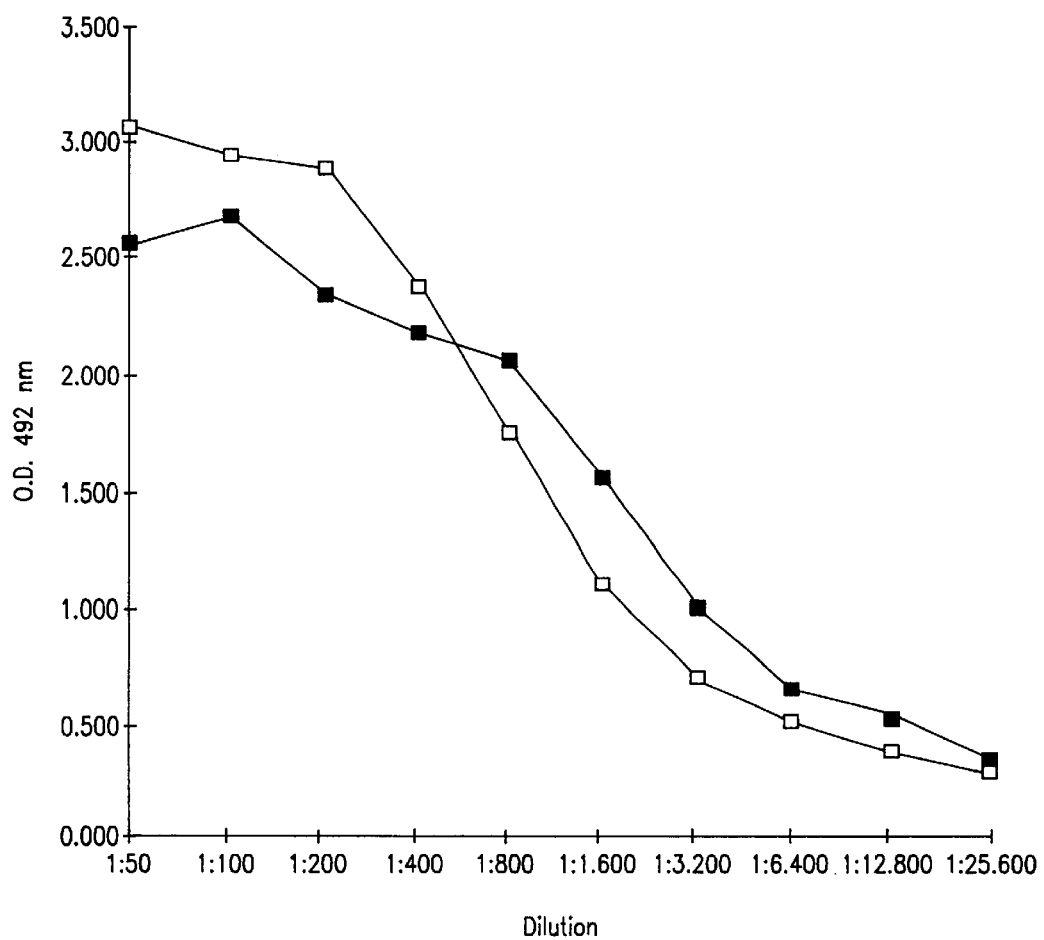
FIG. 9 shows graphically the ELISA results generated in Example 14.
- □ riHBV plate coating
- ■ noHBV plate coating

These results are presented in graph form in FIG. 9.

Example 15

Analysis of Antibody Production and Activity of Antibodies Raised to Peptide Sequences Corresponding to Residues 126–137 of the Surface Protein of the Hepatitis B Virus The following peptide, based on residues 126–137 of the surface protein of the Hepatitis B virus, was synthesized.

noHBV-S(126–137) H-Thr-Thr-Pro-Ala-Gln-Gly-Asn-Ser-Met-Tyr-Pro-Ser-OH (SEQ ID No.12)

A potential T cell epitope was selected from the surface protein, residues 20–33:

H-Phe-Leu-Leu-Thr-Arg-Ile-Leu-Thr-Ile-Pro-Gln-Ser-Leu-Asp-OH (SEQ ID No.13)

These peptides were synthesized on MAP (multiple antigen peptide) resin with eight peptide branches through lysine to each MAP core which was coupled to a cysteine protected by the acetamido methyl group. The side chain protecting groups used were: trityl for glutamine and asparagine, t-butyl for serine, threonine, aspartic acid and tyrosine and 2,2,5,7,8-pentamethyl chroman-6-sulphonyl for arginine. Cleavage and side-chain deprotection of noHBV-S(126–137) were accomplished by reaction of the peptidyl resin for 90 min at room temperature with 10 ml of TFA, 0.25 ml 1,2-ethanedithiol, 0.5 ml thioanisole, 0.5 ml water and 0.75 g phenol. Cleavage and side-chain deprotection of the potential T cell epitope were accomplished by reaction of the peptidyl resin for 90 min at 0° C. with 1M trimethylsilylbromide-thioanisole in TFA, containing 0.25M 1,2-ethanedithiol (Yajima et al., 1988).

Dimerisation of the two MAPs, noHBV-S(126–137) and the potential T cell epitope, in equimolar amounts by oxidation to the disulphide with iodine in acetic acid was carried out by the method of Tam and Lu (1989).

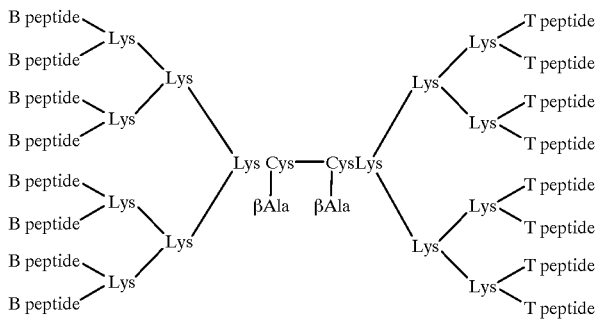

The above construct was emulsified in Freund's complete adjuvant (1:1) and used to immunize white Swiss mice according to the following schedule:

| Day 0: | 20 μg of peptide in 100 μl emulsion, subcutaneous (complete Freund's). |
|---|---|
| Day 10: | 70 μg of peptide in 100 μl emulsion, subcutaneous (incomplete Freund's). |
| Day 20: | 20 μg of peptide in 100 μl emulsion, intraperitoneally (incomplete Freund's). |

The mice (4 in each group) were bled retro-orbitally five days after the last injection and the serum used in ELISA using microtitre plates coated with 1 μg/well of either no-HBV-S(126–137) or ri-HBV-S(126–137) both of them conjugated to BSA.

| | O.D. 492 nm | |
|---|---|---|
| Plate coating: | noHBV-S(126–137) | riHBV-S(126–137) |
| Dilution: | | |
| 1:50 | 2.643 | 2.813 |
| 1:100 | 2.697 | 2.688 |
| 1:200 | 2.528 | 2.293 |
| 1:400 | 1.578 | 1.498 |
| 1:800 | 0.929 | 0.954 |
| 1:1,600 | 0.548 | 0.571 |
| 1:3,200 | 0.374 | 0.387 |
| 1:6,400 | 0.268 | 0.297 |
| 1:12,800 | 0.248 | 0.269 |
| 1:25,600 | 0.198 | 0.249 |

Figure 10:
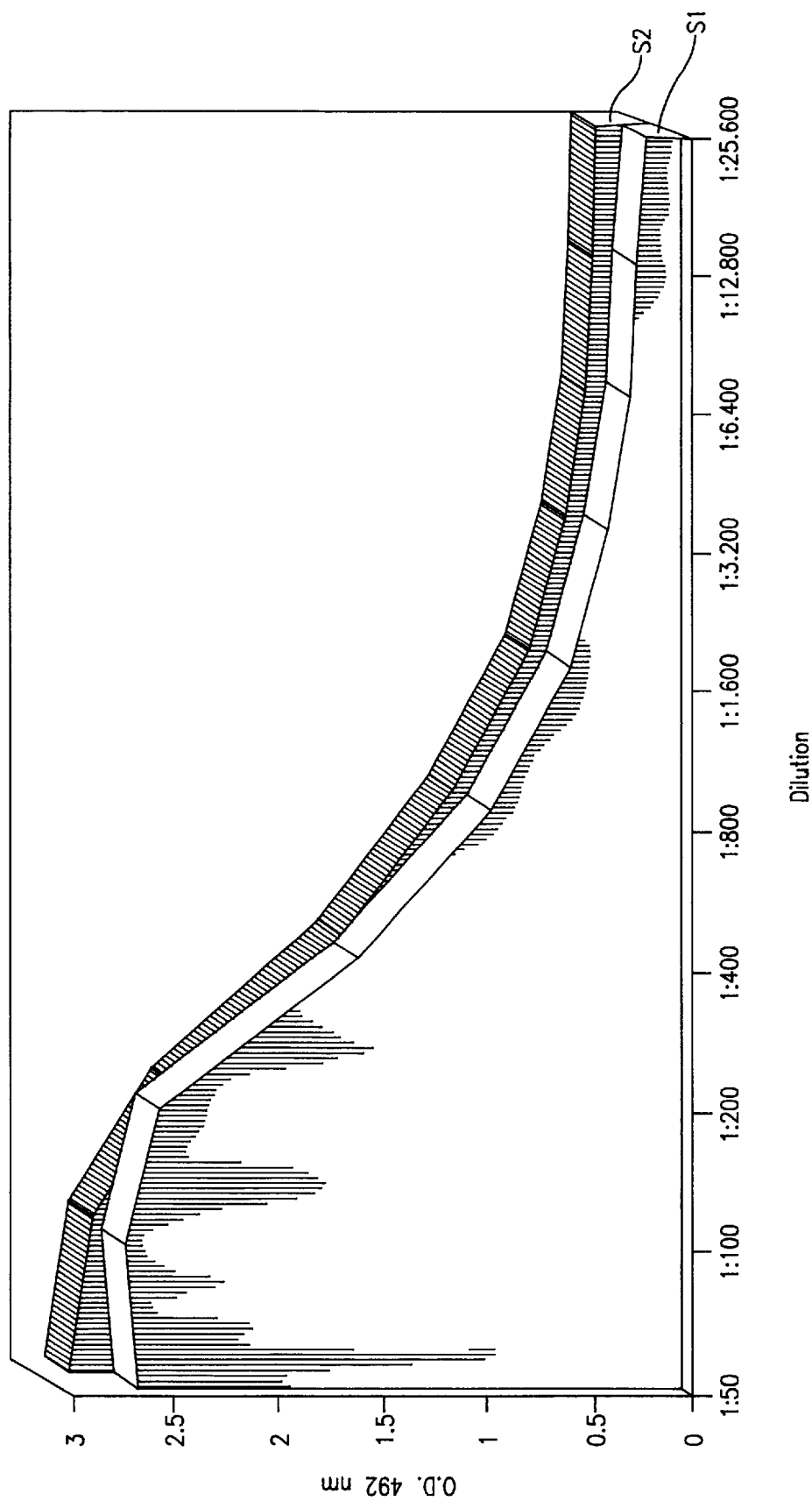
FIG. 10 shows graphically the ELISA results generated in Example 15.
- S1: no-peptide-coated wells
- S2: ri-peptide-coated wells.
Figure 11:
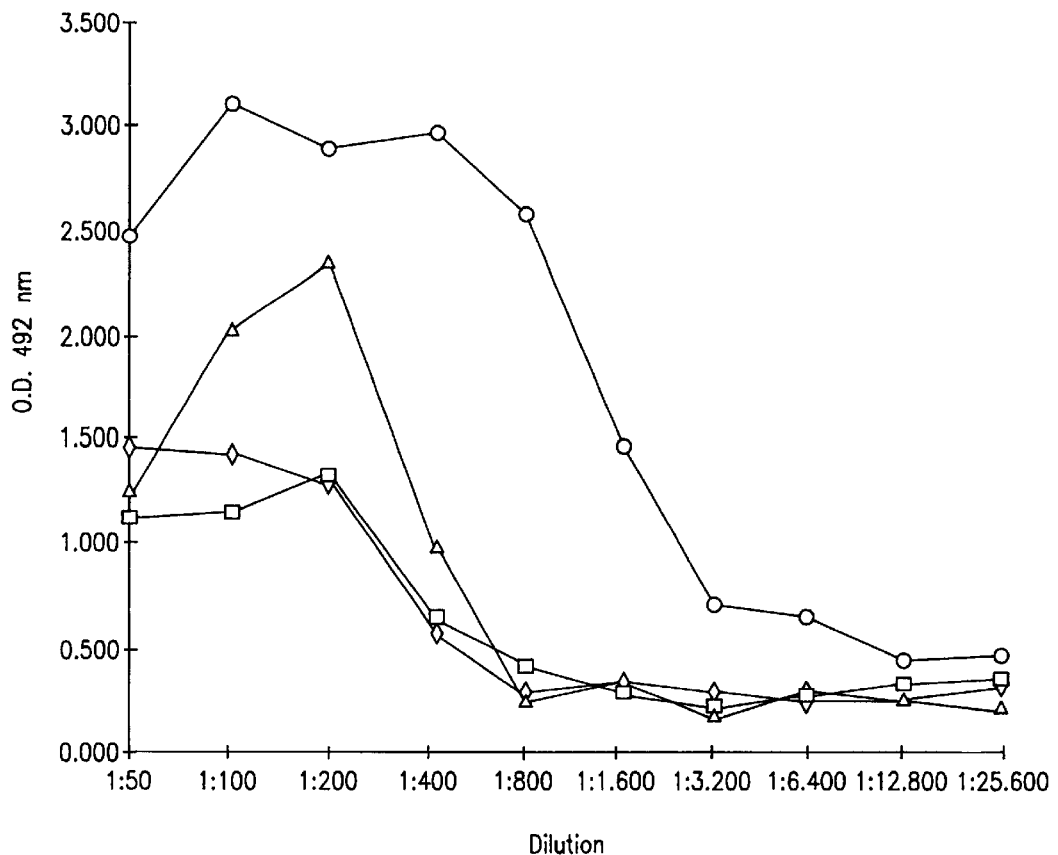
FIG. 11 shows graphically the ELISA results generated in Example 16.
- Bold lines: Antisera to ri-HBV peptide
- Normal lines: Antisera to no-HBV peptide
- Circle and diamond symbols: no-HBV peptide-coated wells.
- Square and triangle symbols: ri-HBV peptide-coated wells.

These results are shown in graph form in FIG. 10.

Example 16

Analysis of Antibody Production and Activity of Antibodies Raised to Peptide Sequences Corresponding to Residues 127–140 of the PreS Protein of the Hepatitis B Virus The following two peptides, based on residues 127–140 of the preS protein of the Hepatitis B virus, were synthesized.
noHBV-PreS(127–140) H-Phe-His-Gln-Thr-Leu-Gln-Asp-Pro-Arg-Val-Arg-Gly-Leu-Tyr-Cys-OH (SEQ ID No.14)
riHBV-PreS(127–140) H-Cys-tyr-leu-Gly-arg-val-arg-pro-asp-gln-leu-thr-gln-his-phe-NH₂

The synthesis of noHBV-PreS(127–140) was carried out on polyamide PepsynKA resin pre-esterified with Fmoc-Cys (trt) and riHBV-PreS(127–140) was on Polyhipe Rink resin. The side chain protecting groups used were: trityl for cysteine, histidine and glutamine, t-butyl for threonine, aspartic acid and tyrosine and 2,2,5,7,8-pentamethyl chroman-6-sulphonyl for arginine. Cleavage and side-chain deprotection were accomplished by reaction of the peptidyl resins for 90 min at 0° C. with 1M trimethylsilylbromide-thioanisole in TFA containing 0.25M 1,2-ethanedithiol (Yajima et al., 1988).

Both peptides were independently conjugated to either KLH or BSA.

The KLH conjugates were emulsified in Freund's complete adjuvant (1:1) and used to immunize white Swiss mice according to the following schedule:

| | |
|---|---|
| Day 0: | 20 μg of peptide in 100 μl emulsion, subcutaneous (complete Freund's). |
| Day 10: | 20 μg of peptide in 100 μl emulsion, subcutaneous (incomplete Freund's). |
| Day 20: | 20 μg of peptide in 100 μl emulsion, intraperitoneally (incomplete Freund's). |

The mice (4 in each group) were bled retro-orbitally five days after the last injection and the serum used in ELISA using microtitre plates coated with 1 μg/well of the appropriate peptide conjugated to BSA.

| | O.D. 492 nm | | | |
|---|---|---|---|---|
| Plate coating: | noHBV-PreS (127–140) | | riHBV-PreS (127–140) | |
| Antiserum to: | no-HBV | ri-HBV | no-HBV | ri-HBV |
| Dilution: | | | | |
| 1:50 | 2.477 | 1.468 | 1.125 | 1.253 |
| 1:100 | 3.108 | 1.425 | 1.150 | 2.035 |
| 1:200 | 2.892 | 1.284 | 1.325 | 2.345 |
| 1:400 | 2.997 | 0.577 | 0.636 | 0.976 |
| 1:800 | 2.582 | 0.269 | 0.409 | 0.248 |
| 1:1,600 | 1.458 | 0.301 | 0.271 | 0.336 |
| 1:3,200 | 0.698 | 0.259 | 0.183 | 0.162 |
| 1:6,400 | 0.638 | 0.217 | 0.256 | 0.283 |
| 1:12,800 | 0.412 | 0.221 | 0.293 | 0.225 |
| 1:25,600 | 0.429 | 0.282 | 0.304 | 0.185 |

These results are presented in graph form in FIG. 11.

Example 17

Analysis of Antibody Production and Activity of Antibodies Raised to Peptide Sequences Corresponding to Residues 127–140 of the preS Protein of the Hepatitis B Virus The following two peptides, based on residues 127–140 of the preS protein of the Hepatitis B virus, were synthesized.

noHBV-PreS(127–140) H-Phe-His-Gln-Thr-Leu-Gln-Asp-Pro-Arg-Val-Arg-Gly-Leu-Tyr-OH (SEQ ID No.15)

ri HBV-PreS (127–140) H-tyr-leu-Gly-arg-val-arg-pro-asp-gln-leu-thr-gln-his-phe-OH A potential T cell epitope was selected from the preS protein, residues 52–64:

H-Trp-Pro-Asp-Ala-Asn-Lys-Val-Gly-Ala-Gly-Ala-Phe-Gly-OH (SEQ ID No.16)

These peptides were synthesized on MAP (multiple antigen peptide) resin with eight peptide branches through lysine to each MAP core which was coupled to a cysteine protected by the acetamido methyl group. The side chain protecting groups used were: trityl for histidine, glutamine and asparagine, t-butyl for threonine and aspartic acid, t-butoxycarbonyl for lysine and 2,2,5,7,8-pentamethyl chroman-6-sulphonyl for arginine. Cleavage and side-chain deprotection of noHBV-PreS(127–140) and ri HBV-PreS (127–140) were accomplished by reaction of the peptidyl resin for 90 min at 0° C. with 1M trimethylsilylbromide-thioanisole in TFA containing 0.25M 1,2-ethanedithiol (Yajima et al., 1988). Cleavage and side-chain deprotection of the potential T cell epitope were accomplished by reaction of the peptidyl resin for 90 min at room temperature with 1,2-ethanedithiol (5% by volume) and water (5% by volume) in TFA.

Dimerization of the two MAPs, noHBV-PreS (127–140) and the potential T cell epitope, in equimolar amounts, by oxidation to the disulphide with iodine in acetic acid, was carried out by the method of Tam and Lu (1989). In a similar way, the two MAPs, ri HBV-PreS (127–140) and noHBV-PreS (52–64) were dimerized.

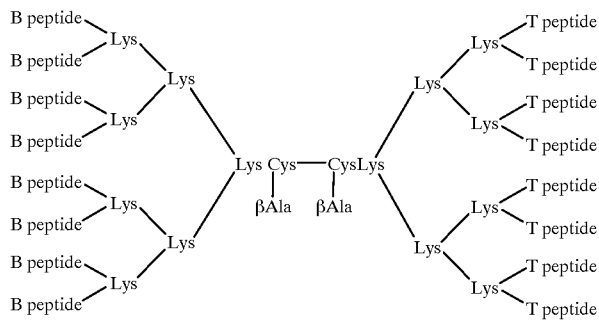

The above constructs were emulsified in Freund's complete adjuvant (1:1) and used to immunize white Swiss mice according to the following schedule:

| Day 0: | 20 μg of peptide in 100 μl emulsion, subcutaneous (complete Freund's). |
| --- | --- |
| Day 10: | 20 μg of peptide in 100 μl emulsion, subcutaneous (incomplete Freund's). |
| Day 20: | 20 μg of peptide in 100 μl emulsion, intraperitoneally (incomplete Freund's). |

The mice (4 in each group) were bled retro-orbitally five days after the last injection and the serum used in ELISA using microtitre plates coated with 1 μg/well of either noHBV-PreS(127–140) or riHBV-PreS(127–140) both of them conjugated to BSA.

| | O.D. 492 nm | | | |
| --- | --- | --- | --- | --- |
| Plate coating: | noHBV-PreS (127–140) | | riHBV-PreS (127–140) | |
| Antiserum to: | no-HBV | ri-HBV | no-HBV | ri-HBV |
| Dilution: | | | | |
| 1:50 | 2.192 | 1.735 | 2.001 | 2.558 |
| 1:100 | 1.900 | 2.111 | 2.121 | 2.457 |
| 1:200 | 2.069 | 2.482 | 1.920 | 2.499 |
| 1:400 | 0.916 | 1.299 | 1.047 | 1.450 |
| 1:800 | 0.325 | 0.454 | 0.685 | 0.751 |
| 1:1,600 | 0.190 | 0.283 | 0.307 | 0.314 |
| 1:3,200 | 0.246 | 0.390 | 0.195 | 0.250 |
| 1:6,400 | 0.275 | 0.224 | 0.261 | 0.244 |
| 1:12,800 | 0.215 | 0.217 | 0.188 | 0.205 |
| 1:25,600 | 0.168 | 0.222 | 0.354 | 0.312 |

Figure 12:
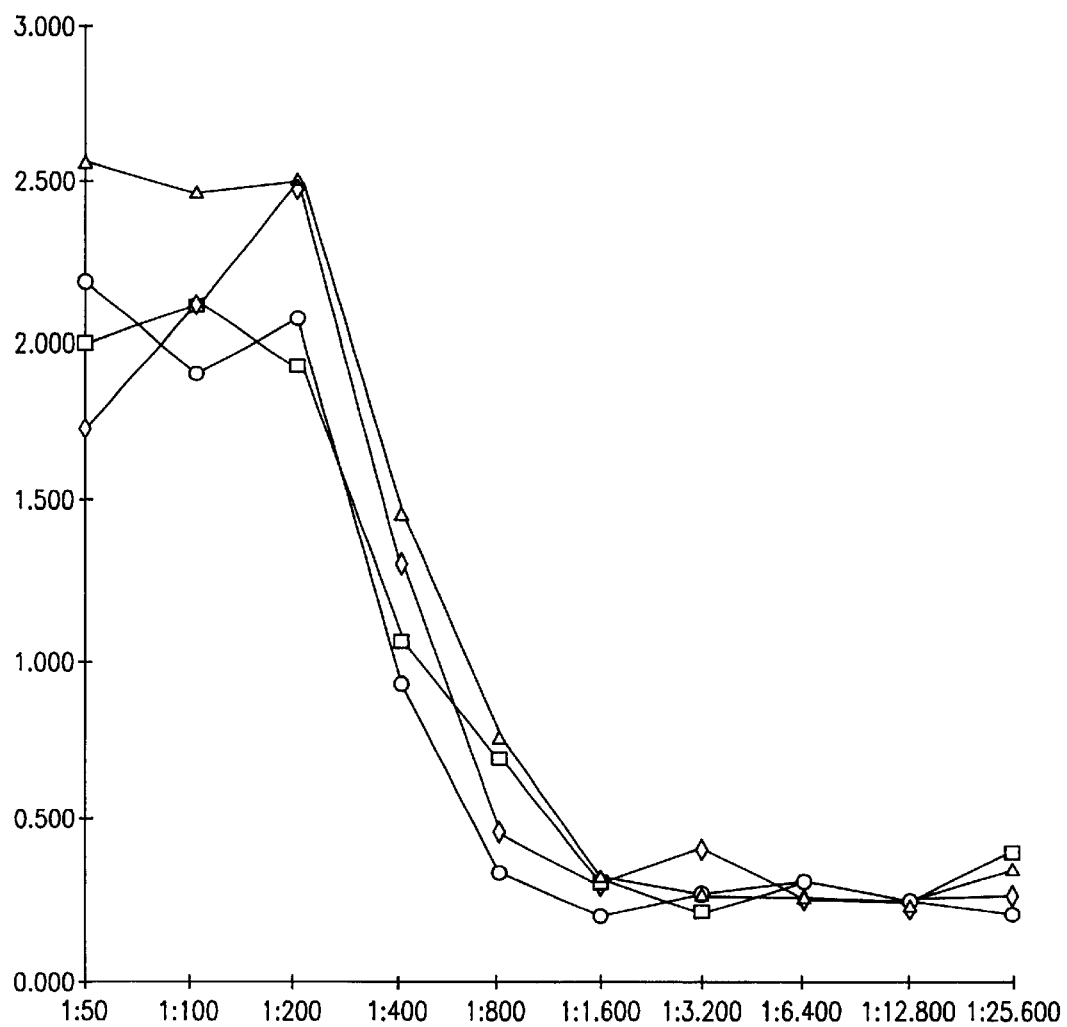
FIG. 12 shows graphically the ELISA results generated in Example 17.
- Bold lines: Antisera to ri-HBV peptide
- Normal lines: Antisera to no-HBV peptide
- Circle and diamond symbols: no-HBV peptide-coated wells.
- Square and triangle symbols: ri-HBV peptide-coated wells.

These results are presented in graph form in FIG. 12.

INDUSTRIAL APPLICATION

Antigen analogues in accordance with the invention have a range of potential applications in eliciting immunogenic responses in a host. These antigen analogues can be used in the treatment and/or prophylaxis of diseases, and drug delivery and therapy of disease states. In particular, these antigen analogues can be used in vaccines in animals, including humans for protection against pathogens and the like.

In addition, the synthetic antigen analogues have the potential to be used as diagnostic tools in assays for detecting the presence of antibodies to native antigens or in research such as investigations into antigen-antibody recognition, specificity, antigenicity and immunogenic response.

Antibodies raised against the antigen analogues of the invention can be used for diagnostic purposes where detection of the native antigen is desired in samples or in the treatment and/or prophylaxis of diseases neutralized by the antibodies, or in drug delivery.

REFERENCES

Arshady, R., Atherton, E., Clive, D. L. J. & Sheppard, R. C. (1981) Peptide synthesis. Part 1. Preparation and use of polar supports based on poly(dimethylacrylamide). J. Chem. Soc. Perkin Trans. I, 529–537.

Atherton. E., Cameron, L. R. & Sheppard, R. C. (1988) Peptide synthesis. Part 10. Use of pentafluorophenyl esters of fluorenylmethoxycarbonylamino acids in solid phase peptide synthesis. Tetrahedron, 44, 843–857.

Bidlingmeyer, B. A., Tarvin, T. L. & Cohen, S. A. (1987) Amino acid analysis of submicrogram hydrolyzate samples. In "Methods in Protein Sequence Analysis", Walsh, K. A. (Ed.), pp. 229–245, The Humana Press.

Bonelli, F., Pessi, A. & Verdini, A. S. (1984) Solid phase synthesis of retro-inverso peptide analogues. Int. J. Peptide Protein Res., 24, 553–556.

Carpino, L. A. & Han, G. Y. (1972) The 9-fluorenylmethoxycarbonyl amino-protecting group. J. Org. Chem., 37, 3404–3409.

Davies, D. R., Sheriff, S. & Padlan, E. A. (1988) Antibody-antigen complexes. J. Biol. Chem., 263,10541–10544.

Eberle, A. N., Atherton, E., Dryland, A. & Sheppard, R. C. (1986) Peptide synthesis. Part 9. Solid-phase synthesis of melanin concentrating hormone using a continuous-flow polyamide method. J. Chem. Soc. Perkin Trans I, 361–367.

Gausepohl, H., Kraft, M. & Frank, R. W. (1989) Asparagine coupling in Fmoc solid phase peptide synthesis. Int. J. Peptide Protein Res., 34, 287–294.

Goodman, M. & Chorev, M. (1981) The synthesis and confirmational analysis of retro-inverso analogues of biologically active molecules. In 'Perspectives in Peptide Chemistry'; Karger, Basel; pp. 283–294.

Hancock, W. S. & Battersby, J. E. (1976) A new micro-test for the detection of incomplete coupling reactions in solid-phase peptide synthesis using 2,4,6-trinitrobenzene-sulphonic acid. Anal. Biochem., 71, 260–264.

Hudson, D. (1988) Methodological implications of simultaneous solid-phase peptide synthesis. 1. Comparison of different coupling procedures. J. Org. Chem., 53, 617–624.

Hunkapillar, M. W. & Hood, L. E. (1983) Protein sequence analysis: automated microsequencing. Science, 219, 650–659.

Lerner, R. A. (1984) Antibodies of predetermined specificity in biology and medicine. Adv. Immunol., 36, 1–44.

Liu, F.-T., Zinnecker, M., Hamaoka, T. & Katz, D. H. (1979) New procedures for preparation and isolation of conjugates of proteins and a synthetic copolymer of D-amino acids and immunochemical characterization of such conjugates. Biochemistry, 18, 690–697.

D. Mazier, S. Mellouk, R. L. Beaudoin, B. Texier, P. Druilhe, W. Hockmeyer, J. Trosper, C. Paul, Y. Charoenvit, J. Young, F. Miltgen, L. Chedid, J. P. Chigot, B. Galley, O. Brandicourt and M. Geutilini (1986). Effect of antibodies on recombinant and synthetic peptides on P. falciparum sporozoites in vitro. Science 231, 158–159.

Arnon R (1991) Synthetic peptides as the basis for vaccine design. Molec. Immunol. 28 209–215.

Pessi, A., Pinori, M., Verdini, A. S. & Viscomi, G. C. (1987) Totally solid phase synthesis of peptide(s)-containing retro-inverted peptide bond, using crosslinked sarcosinyl copolymer as support. European Patent 97994-B, Sep. 30, 1987 (8739).

Tam, J. P. (1988) Acid deprotection reactions in peptide synthesis. In 'Macromolecular Sequencing and Synthesis, Selected Methods and Application', pp. 153–184; Alan R. Liss, Inc.

Verdini, A. S. & Viscomi, G. C. (1985) Synthesis, resolution, and assignment of configuration of potent hypotensive retro-inverso bradykinin potentiating peptide 5a(BPP5a) analogues. J. Chem. Soc. Perkin Trans. I, 697–701.

Yajima, H., Fuji, N., Funakoshi, S., Watanabe, T., Murayama, E. & Otaka, A. (1988) New strategies for the chemical synthesis of proteins. Tetrahedron, 44, 805–819.

P. J. Barr, H. L. Gibson, V. Enea, D. E. Arnot, M. R. Hollingdale & V. Nussenzweig (1987) Expression in yeast of a *Plasmodium vivax* antigen of potential use in a human malaria vaccine. J. Exp. Med., 165, 1160–1171

T. C. Chanh, G. R. Dreesman, P. Kanda, G. P. Linette, J. T. Sparrow, D. D. Ho & R. C. Kennedy (1986) Induction of anti-HIV neutralizing antibodies by synthetic peptides. EMBO J., 5, 3065–3071

J. B. Dame, J. L. Williams, T. F. McCutchan, J. L. Weber, R. A. Wirtz, W. T. Hockmeyer, L. W. Maloy, J. D. Hanes, I. Schneider, D. Roberts, G. S. Sanders, E. P. Reddy, C. L. Diggs & L. H. Miller (1984) Structure of the gene encoding the immunodominant surface antigen on the sporozoite of the human malaria parasite *Plasmodium falciparum*. Science, 225,593

H. M. Etlinger, A. M. Felix, D. Gillessen, E. P. Heimer, M. Just, J. R. L. Pink, F. Sinigaglia, D. Stuerchler, D. Takacs, A. Trzeciak & H. Matile (1988) Assessment in humans of a synthetic peptide-based vaccine against the sporozoite stage of the human malaria parasite, *Plasmodium falciparum*. J. Immunol., 140,626–633

D.A. Herrington, D. F. Clyde, G. Losonsky, M. Cortesia, J. R. Murphy, J. Davis, S. Baqar, A. M. Felix, E. P. Heimer, D. Gillessen, E. Nardin, R. S. Nussenzweig, V. Nussenzweig, M. R. Hollingdale & M. M. Levine (1987) Safety and immunogenicity in man of a synthetic peptide malaria vaccine against *Plasmodium falciparum* sporozoites. Nature, 328,257–259

D. A. Herrington, D. F. Clyde, J. R. Davis, S. Baqar, J. R. Murphy, J. F. Cortese, R. S. Bank, E. Nardin, D. DiJohn, R. S. Nussenzweig, V. Nussenzweig, J. R. Torres, J. Murillo, M Cortesia, D. Stuerchler, M. R. Hollingdale & M. M. Levine (1990) Human studies with synthetic peptide sporozoite vaccine (NANP)$_3$-TT and immunization with irradiated sporozoites. Bull. WHO, 68 (Suppl.), 33–37

P. J. Klasse, R. Pipkorn & J. Blomberg (1988) Presence of antibodies to a putatively immunosuppressive part of human immunodeficiency virus (HIV) envelope glycoprotein gp41 is strongly associated with health among HIV-positive subjects. Proc.Natl.Acad.Sci. USA, 85,5225–5229

M. Mariani, L. Bracci, R. Presentini, D. Nucci, P. Neri & G. Antoni (1987) Immunogenicity of a free synthetic peptide: carrier-conjugation enhances antibody affinity for the native protein. Molec.Immunol., 24,297–303.

E. J. Mylecharane, I. Spence, A. Comis, M. I. Tyler & M. E. H. Howden (1991) Immunization with a synthetic robustoxin derivative lacking disulphide bridges protects anaesthetised monkeys against potentially lethal challenge with male funnel-web spider (*Atrax robustus*) venom. Proceedings of World Congress on Animal, Plant and Microbial Toxins, Singapore (November 1991)

G. M. Nicholson, I. Spence, A. Comis, M. I. Tyler & M. E. H. Howden (1991) Funnel web spider toxins. Toxins and Targets (D. Watters & M. Lavin, Eds.) pp 97–101, Harwood Academic Publishers, Melbourne H. Rink (1987) Solid-phase synthesis of protected peptide fragments using a trialkoxy-diphenyl-methylester resin. Tetrahedron Lett., 28,3787–3790

B. J. Spalding (1992) In hot pursuit of an HIV vaccine. Bio/Technology, 10, 24–29

R. A. Wirtz, J. F. Duncan, E. K. Njelesoni, I. Schneider, A. E. Brown, C. N. Oster, J. B. O. Were and H. K. Webster (1989) Bull WHO, 67,535–542. ELISA method for detecting *Plasmodium falciparum* circumsporozoite antibody.

Steward, M. W. & Howard, C. R. (1987) Synthetic peptides: a next generation of vaccines? Immunol. Today, 8, 51–58.

Jue R., Lambert J. M., Pierce L. R., Traut R. R. (1978) Addition of sulfhydryl groups to *Escherichia coli* ribosomes by protein modification with 2-iminothiolane (methyl 4-mercaptobutyrimidate) Biochem. 17 (25), 5399–5405.

Tam J. P. and Lu Y. A. Vaccine engineering: Enhancement of immunogenicity of synthetic peptide vaccines related to hepatitis in chemically defined models consisting of T- and B-cell epitopes. *Proc. Natl. Acad. Sci USA* (1989) 86 9084–9088.

What is claimed is:

1. A synthetic peptide antigen analogue of a native peptide antigen, wherein said synthetic peptide antigen analogue is retro-inverso modified to contain all D-amino acids with reversed direction of peptide bonds and reversed termini, with respect to the native antigen, and wherein said synthetic peptide antigen analogue is at least five amino acids in length and induces the production of antibodies which recognize the native peptide antigen.

2. A synthetic peptide antigen analogue according to claim 1, wherein the amino acid residues at the amino terminus of the retro-inverted sequences are substituted by side-chain-analogous α-substituted germinal-diaminomethanes and malonates at the carboxy terminus.

3. A synthetic peptide antigen analogue according to claim 1 wherein the native antigen is a naturally occurring polypeptide or antigenic fragment thereof.

4. A synthetic peptide antigen analogue according to claim 1 wherein the antigen analogue is selected from the group consisting of an analogue of the immunodominant epitope of the circumsporozoite coat protein of P. falciparum sporozoites; a diphtheria toxin antigen; robustoxin; a hepatitis virus antigen; and an HIV antigen.

5. The synthetic peptide antigen analogue according to claim 4, wherein said antigen analogue is a retro-inverso analogue of a P. falciparum sporozoite protein having a sequence selected from the group consisting of SEQ ID NO:3 and SEQ ID NO:4.

6. The synthetic peptide antigen analogue according to claim 4, wherein said antigen analogue is a retro-inverso analogue of a diphtheria toxin antigen having a sequence of SEQ ID NO:5.

7. The synthetic peptide antigen analogue according to claim 4, wherein said antigen analogue is a retro-inverso analogue of an HIV antigen having a sequence selected from the group consisting of SEQ ID NO: 6, SEQ ID NO:7, and SEQ ID NO: 10.

8. The synthetic peptide antigen analogue according to claim 4, wherein said antigen analogue is a retro-inverso analogue of a hepatitis C virus antigen having a sequence selected from the group consisting of SEQ ID NO: 8 and SEQ ID NO:9.

9. The synthetic peptide antigen analogue according to claim 4, wherein said antigen analogue is a retro-inverso analogue of a hepatitis B virus antigen having a sequence selected from the group consisting of SEQ ID NO: 11 and SEQ ID NO: 14.

10. The synthetic peptide antigen analogue according to claim 4, wherein said antigen analogue is a retro-inverso analogue of robustoxin.

11. A synthetic peptide antigen analogue according to claim 1 which is capable of eliciting an immune response which lasts longer than the immune response obtained with the corresponding native antigen.

12. A method of preparing a synthetic peptide antigen analogue of a native peptide antigen, comprising synthesizing a retro-inverso antigen analogue according to claim 1.

13. The method according to claim 12 which method additionally comprises conjugating the synthetic peptide antigen analogue to a suitable carrier molecule.

14. A method of preparing an immunogenic composition against a native peptide antigen comprising providing a synthetic peptide antigen analogue of the native peptide antigen according to claim 1 and admixing an effective amount of the synthetic peptide antigen analogue with a pharmaceutically or veterinarally acceptable carrier, diluent, excipient and/or adjuvant.

15. A composition comprising a synthetic peptide antigen analogue according to claim 1 and a physiologically compatible carrier.

16. A method of inducing antibodies to a native antigenic peptide, said method comprising the step of delivering to a subject a synthetic peptide antigen according to claim 1.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: YES (iv) ANTI-SENSE: NO (x) PUBLICATION INFORMATION:
      (H) DOCUMENT NUMBER: AU PL4374
      (I) FILING DATE: 27-AUG-1992

(xi) SEQUENCE DESCRIPTION: SEQ ID NO: 1:

Gly Cys Gly Pro Leu Ala Gln Pro Leu Ala Gln Gly
1               5                   10

(2) INFORMATION FOR SEQ ID NO: 2:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: YES (x) PUBLICATION INFORMATION:
      (H) DOCUMENT NUMBER: AU PL4374
      (I) FILING DATE: 27-AUG-1992

(xi) SEQUENCE DESCRIPTION: SEQ ID NO: 2:

Gly Gln Ala Leu Pro Gln Ala Leu Pro Gly Cys Gly
1               5                   10

(2) INFORMATION FOR SEQ ID NO: 3:

(i) SEQUENCE CHARACTERISTICS:
      (A) LENGTH: 13 amino acids
      (B) TYPE: amino acid
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Plasmodium falciparum
             (D) DEVELOPMENTAL STAGE: SPOROZOITE (ix) FEATURE:
             (A) NAME/KEY: Modified-site
             (B) LOCATION: 1..2
             (D) OTHER INFORMATION: /label= A
                 /note= "RESIDUE 1 IS AN EXTRA CYSTEINE
                 RESIDUE ADDED TO THE N-TERMINUS OF THE
                 PEPTIDE"

(x) PUBLICATION INFORMATION:
             (H) DOCUMENT NUMBER: AU PL4374
             (I) FILING DATE: 27-AUG-1992

(xi) SEQUENCE DESCRIPTION: SEQ ID NO: 3:

Cys Asn Ala Asn Pro Asn Ala Asn Pro Asn Ala Asn Pro
1               5                  10

(2) INFORMATION FOR SEQ ID NO: 4:

(i) SEQUENCE CHARACTERISTICS:
             (A) LENGTH: 12 amino acids
             (B) TYPE: amino acid
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Plasmodium falciparum
             (D) DEVELOPMENTAL STAGE: SPOROZOITE (x) PUBLICATION INFORMATION:
             (H) DOCUMENT NUMBER: AU PL4374
             (I) FILING DATE: 27-AUG-1992

(xi) SEQUENCE DESCRIPTION: SEQ ID NO: 4:

Asn Ala Asn Pro Asn Ala Asn Pro Asn Ala Asn Pro
1               5                  10

(2) INFORMATION FOR SEQ ID NO: 5:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Corynebacterium diphtheriae (x) PUBLICATION INFORMATION:
             (H) DOCUMENT NUMBER: AU PL4374
             (I) FILING DATE: 27-AUG-1992

(xi) SEQUENCE DESCRIPTION: SEQ ID NO: 5:

```
Gly Asn Arg Val Arg Arg Ser Val Gly Ser Ser Leu Lys Cys
1               5                   10
```

(2) INFORMATION FOR SEQ ID NO: 6:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Human immunodeficiency virus type 1

(ix) FEATURE:
        (A) NAME/KEY: Modified-site
        (B) LOCATION: 18..19
        (D) OTHER INFORMATION: /label= A
            /note= "THE C TERMINAL AMINO ACID OF THIS
            PEPTIDE HAS BEEN AMIDATED. THE ENTIRE
            PEPTIDE IS BASED ON AMINO ACIDS 735-753 OF
            THE PROTEIN gp41 OF HIV1."

(x) PUBLICATION INFORMATION:
        (H) DOCUMENT NUMBER: AU PL4374
        (I) FILING DATE: 27-AUG-1992

(xi) SEQUENCE DESCRIPTION: SEQ ID NO: 6:

```
Tyr Asp Arg Pro Glu Gly Ile Glu Glu Glu Gly Gly Glu Arg
1               5                   10

Asp Arg Asp Arg Ser
15
```

(2) INFORMATION FOR SEQ ID NO: 7:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Human immunodeficiency virus type 1

(ix) FEATURE:
        (A) NAME/KEY: Modified-site
        (B) LOCATION: 16..17
        (D) OTHER INFORMATION: /label= B
            /note= "THE C TERMINAL RESIDUE OF THIS
            PEPTIDE IS AMIDATED. THE ENTIRE PEPTIDE IS
            BASED ON AMINO ACIDS 583-599 OF PROTEIN gp41
            OF HIV1"

(x) PUBLICATION INFORMATION:
        (H) DOCUMENT NUMBER: AU PL4374
        (I) FILING DATE: 27-AUG-1992

(xi) SEQUENCE DESCRIPTION: SEQ ID NO: 7:

```
Leu Gln Ala Arg Ile Leu Ala Val Glu Arg Tyr Leu Lys
1               5                   10
```

```
Asp Gln Gln Leu
    15

(2) INFORMATION FOR SEQ ID NO: 8:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: HEPATITIS C VIRUS (ix) FEATURE:
        (A) NAME/KEY: Region
        (B) LOCATION: 1..25
        (D) OTHER INFORMATION: /label= A
            /note= "THIS PEPTIDE CORRESPONDS TO AMINO
            ACIDS 306-330 OF THE ENVELOPE PROTEIN FROM
            HCV."

(x) PUBLICATION INFORMATION:
        (H) DOCUMENT NUMBER: AU PL4374
        (I) FILING DATE: 27-AUG-1992

(xi) SEQUENCE DESCRIPTION: SEQ ID NO: 8:

Cys Ser Ile Tyr Pro Gly His Ile Thr Gly His Arg Met
1               5                   10

Ala Trp Asp Met Met Met Asn Trp Ser Pro Thr Ala
    15                  20                  25

(2) INFORMATION FOR SEQ ID NO: 9:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: HEPATITIS C VIRUS (ix) FEATURE:
        (A) NAME/KEY: Region
        (B) LOCATION: 1..37
        (D) OTHER INFORMATION: /label= A
            /note= "THIS PEPTIDE CORRESPONDS TO AMINO
            ACIDS 39-74 OF THE CAPSID PROTEIN OF HCV."

(x) PUBLICATION INFORMATION:
        (H) DOCUMENT NUMBER: AU PL4374
        (I) FILING DATE: 27-AUG-1992

(xi) SEQUENCE DESCRIPTION: SEQ ID NO: 9:

Cys Arg Arg Gly Pro Arg Leu Gly Val Arg Ala Thr Arg
1               5                   10

Lys Thr Ser Glu Arg Ser Gln Pro Arg Gly Arg Arg Gln
```

```
                   15                  20                  25
Pro Ile Pro Lys Val Arg Arg Pro Glu Gly Arg
                30                  35
```

(2) INFORMATION FOR SEQ ID NO: 10:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Human immunodeficiency virus type 1

(ix) FEATURE:
        (A) NAME/KEY: Modified-site
        (B) LOCATION: 20..26
        (D) OTHER INFORMATION: /label= A
            /note= "FOR RESIDUES 20 AND 26 Xaa
            REPRESENTS AMINOBUTYRIC ACID. THE ENTIRE
            PEPTIDE IS BASED ON RESIDUES 579-611 OF THE
            ENVELOPE PROTEIN OF HIV1."

(x) PUBLICATION INFORMATION:
        (H) DOCUMENT NUMBER: AU PL4374
        (I) FILING DATE: 27-AUG-1992

(xi) SEQUENCE DESCRIPTION: SEQ ID NO: 10:

```
Arg Ile Leu Ala Val Glu Arg Tyr Leu Lys Asp Gln Gln
1               5                   10

Leu Leu Gly Ile Trp Gly Xaa Ser Gly Lys Leu Ile Xaa
        15                  20                  25

Thr Thr Ala Val Pro Trp Asn Cys
                30
```

(2) INFORMATION FOR SEQ ID NO: 11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Hepatitis B virus (ix) FEATURE:
        (A) NAME/KEY: Modified-site
        (B) LOCATION: 1..2
        (D) OTHER INFORMATION: /label= A
            /note= "THE PEPTIDE IS MODIFIED AT ITS N
            TERMINUS BY RESIDUES CYS-LYS. RESIDUES
            3-14
            ARE AMINO ACIDS 126-137 OF HBV SURFACE
            PROTEIN."

(x) PUBLICATION INFORMATION:
        (H) DOCUMENT NUMBER: AU PL4374

```
        (I) FILING DATE: 27-AUG-1992

(xi) SEQUENCE DESCRIPTION: SEQ ID NO: 11:

Cys Lys Thr Thr Pro Ala Gln Gly Asn Ser Met Tyr Pro Ser
1               5                   10

(2) INFORMATION FOR SEQ ID NO: 12:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: HEPATITIS B VIRUS (ix) FEATURE:
         (A) NAME/KEY: Region
         (B) LOCATION: 1..12
         (D) OTHER INFORMATION: /label= A
             /note= "THIS PEPTIDE CORRESPONDS TO RESIDUES
             126-137 OF HBV SURFACE PROTEIN."

(x) PUBLICATION INFORMATION:
         (H) DOCUMENT NUMBER: AU PL4374
         (I) FILING DATE: 27-AUG-1992

(xi) SEQUENCE DESCRIPTION: SEQ ID NO: 12:

Thr Thr Pro Ala Gln Gly Asn Ser Met Tyr Pro Ser
1               5                   10

(2) INFORMATION FOR SEQ ID NO: 13:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Hepatitis B virus (ix) FEATURE:
         (A) NAME/KEY: Region
         (B) LOCATION: 1..14
         (D) OTHER INFORMATION: /label= A
             /note= "THIS PEPTIDE CORRESPONDS TO AMINO
             ACIDS 20-33 OF THE SURFACE PROTEIN OF HBV."

(x) PUBLICATION INFORMATION:
         (H) DOCUMENT NUMBER: AU PL4374
         (I) FILING DATE: 27-AUG-1992

(xi) SEQUENCE DESCRIPTION: SEQ ID NO: 13:

Phe Leu Leu Thr Arg Ile Leu Thr Ile Pro Gln Ser Leu Asp
1               5                   10

(2) INFORMATION FOR SEQ ID NO: 14:
```

```
        (i) SEQUENCE CHARACTERISTICS:
            (A) LENGTH: 15 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Hepatitis B virus (ix) FEATURE:
            (A) NAME/KEY: Region
            (B) LOCATION: 1..15
            (D) OTHER INFORMATION: /label= A
                /note= "THIS PEPTIDE CORRESPONDS TO AMINO
                ACIDS 127-140 OF THE PRE S PROTEIN OF HBV
                MODIFIED BY THE ADDITION OF A CYS RESIDUE
                TO
                ITS C TERMINUS."

(x) PUBLICATION INFORMATION:
            (H) DOCUMENT NUMBER: AU PL4374
            (I) FILING DATE: 27-AUG-1992

(xi) SEQUENCE DESCRIPTION: SEQ ID NO: 14:

Phe His Gln Thr Leu Gln Asp Pro Arg Val Arg Gly Leu
1               5                   10

Tyr Cys
    15

(2) INFORMATION FOR SEQ ID NO: 15:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Hepatitis B virus (ix) FEATURE:
            (A) NAME/KEY: Region
            (B) LOCATION: 1..14
            (D) OTHER INFORMATION: /label= A
                /note= "THIS PEPTIDE CORRESPONDS TO RESIDUES
                127-140 OF THE PRE S PROTEIN OF HBV."

(x) PUBLICATION INFORMATION:
            (H) DOCUMENT NUMBER: AU PL4374
            (I) FILING DATE: 27-AUG-1992

(xi) SEQUENCE DESCRIPTION: SEQ ID NO: 15:

Phe His Gln Thr Leu Gln Asp Pro Arg Val Arg Gly Leu Tyr
1               5                   10

(2) INFORMATION FOR SEQ ID NO: 16:

(i) SEQUENCE CHARACTERISTICS:
            (A) LENGTH: 13 amino acids
```

```
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: HEPATITIS B VIRUS (ix) FEATURE:
            (A) NAME/KEY: Region
            (B) LOCATION: 1..13
            (D) OTHER INFORMATION: /label= A
                /note= "THIS PEPTIDE CORRESPONDS TO AMINO
                ACIDS 52-64 OF THE PRE S PROTEIN OF HBV."

(x) PUBLICATION INFORMATION:
            (H) DOCUMENT NUMBER: AU PL4374
            (I) FILING DATE: 27-AUG-1992

(xi) SEQUENCE DESCRIPTION: SEQ ID NO: 16:

Trp Pro Asp Ala Asn Lys Val Gly Ala Gly Ala Pro Gly
1               5                   10
```